United States Patent
Boger

(10) Patent No.: US 9,611,271 B2
(45) Date of Patent: Apr. 4, 2017

(54) C20' UREA DERIVATIVES OF VINCA ALKALOIDS

(71) Applicant: The Scripps Research Institute, LaJolla, CA (US)

(72) Inventor: Dale Boger, LaJolla, CA (US)

(73) Assignee: SCRIPPS RESEARCH INSTITUTE, Lajolla, CA (US)

( * ) Notice: Subject to any disclaimer, the term of this patent is extended or adjusted under 35 U.S.C. 154(b) by 0 days.

(21) Appl. No.: 14/648,624

(22) PCT Filed: Aug. 23, 2013

(86) PCT No.: PCT/US2013/056459
§ 371 (c)(1),
(2) Date: May 29, 2015

(87) PCT Pub. No.: WO2014/088657
PCT Pub. Date: Jun. 12, 2014

(65) Prior Publication Data
US 2015/0291610 A1 Oct. 15, 2015

Related U.S. Application Data

(60) Provisional application No. 61/732,687, filed on Dec. 3, 2012.

(51) Int. Cl.
*C07D 519/04* (2006.01)
*C07D 487/18* (2006.01)
*C07D 471/14* (2006.01)
*C07D 471/22* (2006.01)

(52) U.S. Cl.
CPC ......... *C07D 487/18* (2013.01); *C07D 471/14* (2013.01); *C07D 471/22* (2013.01); *C07D 519/04* (2013.01)

(58) Field of Classification Search
None
See application file for complete search history.

(56) References Cited

U.S. PATENT DOCUMENTS 4,322,351 A 3/1982 Miller et al.
8,940,754 B2 1/2015 Boger

OTHER PUBLICATIONS

Wermuth. The Practice of Medicinal Chemistry, 1996, 203-237.*
Leggans et al., *Org. Lett.* 2012 14:1428-1431.
Leggans et al., *J Med Chem* 2013 56(3):628-639.
Silvestri J Med Chem 2013 56(3):625-627.
Supplementary European Search Report—EP 13 86 0128.
Noller, *Chemistry of Organic Compounds*, 3$^{rd}$ ed., W. B. Saunders Co., Philadelphia, (1965) pp. 307 and 349-350.
*Hawley's Condensed Chemical Dictionary*, Revised by R. L. Lewis, Jr., Van Nostrand Reinhold Co., New York, (1993) pp. 21-22, and 35.
Gotoh et al., *ACS Med. Chem. Lett.* 2011 2:948-952.
Gigant et al., *Nature* 2005 435:519-522.
Carney et al., *Proc Natl Acad Sci*, USA, Aug. 30, 2016 113(35):9691-9698.

* cited by examiner

*Primary Examiner* — Noble Jarrell
(74) *Attorney, Agent, or Firm* — Husch Blackwell LLP

(57) ABSTRACT

A vinca alkaloid compound that is substituted at the 20'-position with a urea or thiourea group is disclosed. The urea's proximal nitrogen atom bonded to the 20'-position carbon atom is secondary, whereas the distal nitrogen atom can be unsubstituted only when the compound contains an optionally present 10'-fluoro substituent, and is otherwise preferably mono- or di-substituted. Methods of preparing the compounds are disclosed as are compositions for their use and methods of treatment using a compound.

23 Claims, No Drawings

C20' UREA DERIVATIVES OF VINCA ALKALOIDS

CROSS-REFERENCE TO RELATED APPLICATION

This application claims priority from provisional application No. 61/732,687 filed Dec. 3, 2012, whose disclosures are incorporated herein by reference.

GOVERNMENTAL SUPPORT

This invention was made with governmental support under CA115526 and 42056 awarded by the National Institutes of Health. The government has certain rights in the invention.

BACKGROUND ART

Vinca alkaloids, originally isolated from the leaves of the periwinkle plant [Vinca rosea Linn., now Cantharanthus roseus (L.) G. Don] [Noble et al., Ann. N. Y. Acad. Sci. 1958 76:882-894; Noble, Lloydia 1964 27:280-281; Svoboda et al., J. Am. Pharm. Assoc. Sci. Ed. 1959 48:659-666] are a family of indole-indoline dimeric compounds that contain a four-ring system containing an indole linked to a five-ring system containing an indoline. Vinca alkaloids can be viewed as a hydration product of the coupling of vindoline with catharanthine. [See, Ishikawa et al., J. Am. Chem. Soc. 2008, 130:420; Ishikawa et al., J. Am. Chem. Soc. 2009, 131:4904.] That hydration provides the 21'-hydroxyl group that is present in vinblastine (1), vincristine (2) and vindestine (1a), below.

Vinblastine and vincristine are the most widely recognized members of the vinca alkaloids as a result of their clinical use as antitumor drugs, and their discovery represent one of the earliest important contributions that plant-derived natural products have made to cancer chemotherapy. [Neuss et al., In The Alkaloids; Brossi et al. Eds.; Academic: San Diego, 1990 37:229-240; Pearce, In The Alkaloids; Brossi et al. Eds.; Academic: San Diego, 1990 37:145-204; Kuehne, In The Alkaloids; Brossi et al. Eds.; Academic: San Diego, 1990 37:77-132.] In particular, those two natural alkaloids, vinblastine and vincristine, are important clinical agents and are used in combination therapies for treatment of Hodgkin's disease, testicular cancer (80% cure rate), ovarian cancer, breast cancer, head and neck cancer, and non-Hodgkin's lymphoma (vinblastine) or are used in the curative treatment regimes for childhood lymphocytic leukemia and Hodgkin's disease (vincristine). The semi-synthetic vinca alkaloid vindesine (1a), a derivative of vinblastine, is used to treat lung cancer and acute leukemia and less often for melanoma, and breast cancer. [Goodman & Gilman's The Pharmaceutical Basis of Therapeutics, Hardman et al. Eds., 9th ed. McGraw-Hill, 1257-1260, 1996.] The limitation to their continued clinical use is the instances of treatment relapse with the emergence of tumor resistance derived from overexpression of P-glycoprotein (Pgp), a cell surface drug efflux transporter that lowers intracellular concentrations of many chemotherapeutic drugs including vinblastine and vincristine.

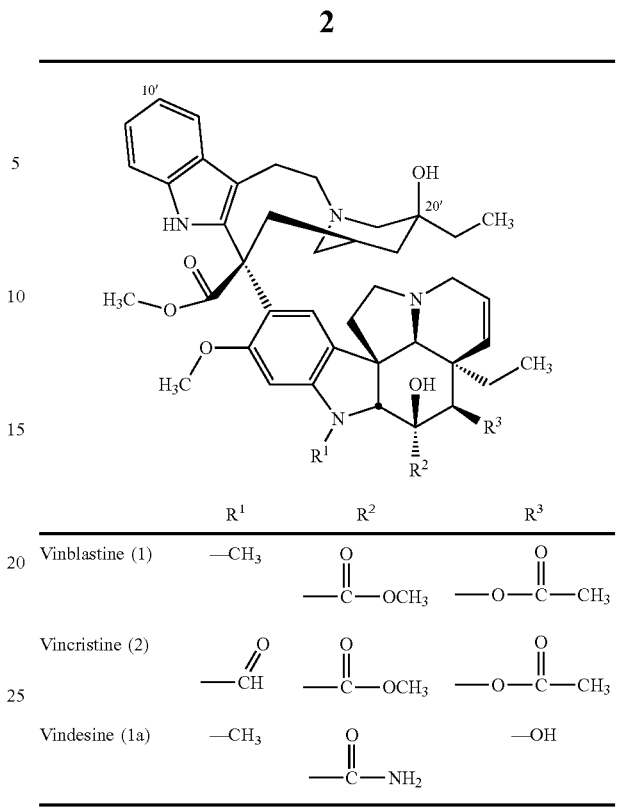

Vinblastine and vincristine were among the first small molecules shown to bind tubulin and to inhibit microtubule formation and mitosis. [Neuss et al., In The Alkaloids; Brossi et al. Eds.; Academic: San Diego, 1990 37:229-240; Pearce, In The Alkaloids; Brossi et al. Eds.; Academic: San Diego, 1990 37:145-204; Kuehne, In The Alkaloids; Brossi et al. Eds.; Academic: San Diego, 1990 37:77-132; Fahy, Curr. Pharm. Design 2001, 7:1181-1197; Potier, J. Nat. Prod. 1980 43:72-86; Kutney, Acc. Chem. Res. 1993 26:559-566; Miyazaki et al., Org. Lett. 2007 9:4737-4740.] Due to their clinical importance, low natural abundance, and structural complexity, they have been the subject of extensive and continuing biological and synthetic investigations. [Fahy, Curr. Pharm. Design 2001, 7:1181-1197; Potier, J. Nat. Prod. 1980 43:72-86; Kutney, Acc. Chem. Res. 1993 26:559-566; Miyazaki et al., Org. Lett. 2007 9:4737-4740; Noble et al., Ann. N. Y. Acad. Sci. 1958 76:882-894; Noble, Lloydia 1964 27:280-281; Svoboda et al., J. Am. Pharm. Assoc. Sci. Ed. 1959 48:659-666; Langlois et al., J. Am. Chem. Soc. 1976 98:7017-7024; Kuehne et al., J. Org. Chem. 1991 56:513-528; Bornmann et al., J. Org. Chem. 1992 57:1752-1760; Yokoshima et al., J. Am. Chem. Soc. 2002 124:2137-2139; Kuboyama et al., Proc. Natl. Acad. Sci. USA 2004 101:11966-11970; Ishikawa et al., J. Am. Chem. Soc. 2008 130:420-421; Ishikawa et al., J. Am. Chem. Soc. 2009 131:4904-4916.]

The vinca alkaloids share a common binding site on tubulin. The relative overall affinities for beta-tubulin binding are vincristine>vinblastine>vinorelbine>vinflunine, but there is no significant difference in the affinity of all four drugs for tubulin heterodimers. Vinflunine is not very potent in vitro yet is active in vivo, and this has been attributed to its superior cellular uptake.

Although these compounds are active in inhibiting the growth of cancerous cells, there are also differences in the profile of efficacy of vinca alkaloids. Vincristine has found wide use in the treatment of hematologic malignancies including leukemias and lymphomas. It is also widely used in pediatric solid tumors and, in the past, in small cell lung cancer. Vinblastine is an important component of the combination regimen that is curative for testicular cancer. Vindesine is used in the treatment of leukemia, lymphoma, melanoma, breast cancer, and lung cancer. Vinorelbine is quite different and has found use mainly in breast cancer and non-small cell lung cancer. Structural formulas for vinblastine, vincristine and vindesine are shown below.

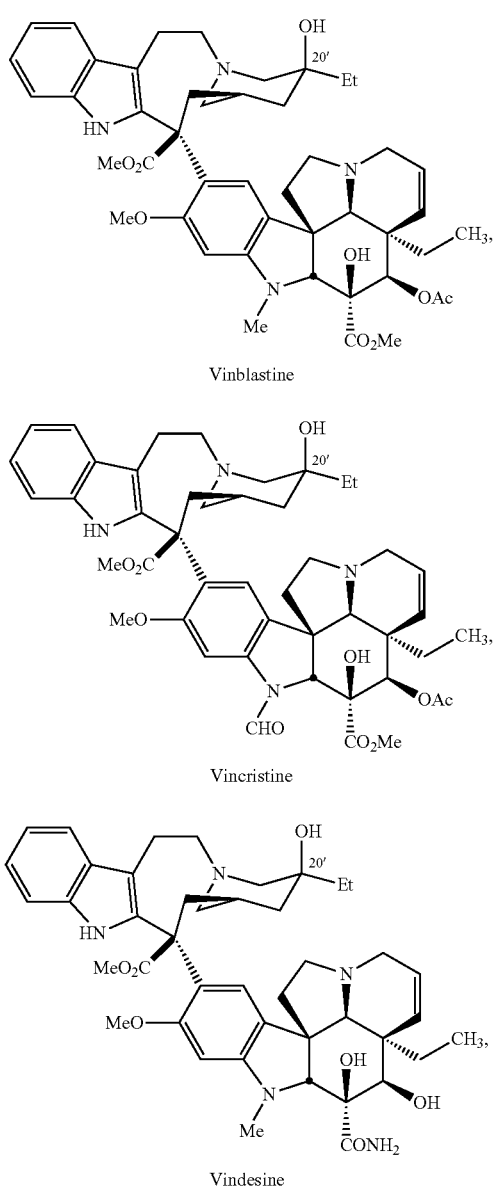

Vinblastine

Vincristine

Vindesine

Cellular growth inhibition data against a leukemia cell line (L1210), a colorectal carcinoma cell line (HCT116) and a vinblastine-resistant colorectal carcinoma cell line (HCT116/VM46) for vinblastine and initial C20'-vinblastine analogues were reported by the present inventor and co-workers in Leggans et al., *Org. Lett.* 2012 14:1428-1431, and are illustrated below.

1, X = OH
Vinblastine

| Compound | IC$_{50}$ (nM) | | |
|---|---|---|---|
| X = | L1210 | HCT116 | HCT116/VM46 |
| OH | 6.0 | 6.8 | 600 |
| H | 50 | 60 | 600 |
| N$_3$ | 670 | 690 | 5500 |
| TEMPO | 4000 | 3800 | 5600 |
| SCN | 560 | 550 | 2900 |
| NH$_2$ | 640 | 600 | >10000 |
| NHCHO | 65 | 85 | 6500 |
| NHCOCH$_3$ | 65 | 90 | 7500 |
| NHCOCF$_3$ | 660 | 690 | 8100 |
| NHCO$_2$CH$_3$ | 50 | 75 | 2600 |
| NHCONHCOCCl$_3$ | 45 | 6.0 | 1600 |
| NHCONH$_2$ | 40 | 7.5 | 4400 |
| NHCSNH$_2$ | 55 | 7.7 | 2000 |
| NCS | 590 | 530 | 7000 |

The present inventor and co-workers reported the total synthesis of vinblastine [Ishikawa et al., *J. Am. Chem. Soc.* 2008 130:420-421; Ishikawa et al., *J. Am. Chem. Soc.* 2009 131:4904-4916] and its extension to the total synthesis of related natural products including vincristine and key analogues that utilizes a one-pot, two-step, biomimetic Fe(III)-promoted single electron oxidative coupling of catharanthine and vindoline and a subsequent Fe(III)/NaBH$_4$-mediated in situ alkene oxidation to generate vinblastine directly. [Ishikawa et al., *J. Am. Chem. Soc.* 2006 128: 10596-10612; Elliott et al., *J. Am. Chem. Soc.* 2006 128: 10589-10595; Choi et al., *Org. Lett.* 2005 7:4539-4542; Yuan et al., *Org. Lett.* 2005 7:741-744; Wilkie et al., *J. Am. Chem. Soc.* 2002 124:11292-11294; Va et al., *J. Am. Chem. Soc.* 2010 132:8489-8495; Sasaki et al., *J. Am. Chem. Soc.* 2010 132:13533-13544; Kato et al., *J. Am. Chem. Soc.* 2010 132:3685-3687; *Bioorg. Med. Chem. Lett.* 2010 20:6408-6410; Gotoh et al., *ACS Med. Chem. Lett.* 2011 2:948-952; Gotoh et al., *J. Am. Chem. Soc.* 2012:134:13240-13243.]

Recently, the inventor and co-workers detailed the results of investigation of the Fe(III)/NaBH$_4$-mediated free radical oxidation of the anhydrovinblastine trisubstituted alkene used to introduce the vinblastine C20'-tertiary alcohol [Ishikawa et al., *J. Am. Chem. Soc.* 2009 131:4904-4916], extending the reaction to provide a simple method for direct functionalization of unactivated alkenes. [Leggans et al., *Org. Lett.* 2012, 14:1428-1431; Barker et al., *J. Am. Chem. Soc.* 2012, 134:13588-13591.] In those studies, the broad alkene substrate scope was defined, the exclusive Markovnikov addition regioselectivity was established, the excellent functional group tolerance was revealed, alternative free radical traps were introduced, the Fe(III) salt and initiating hydride source were examined, and remarkably mild reaction conditions (0-25° C., 5-30 minutes) were introduced that are relatively insensitive to the reaction parameters.

The interest in this Fe(III)/NaBH$_4$-mediated reaction emerged not only from its use in accessing vinblastine, but the opportunity it presented for the late-stage, divergent [Boger et al., *J. Org. Chem.* 1984, 49:4050-4055] preparation of otherwise inaccessible vinblastine analogues incorporating alternative C20'-functionality. Although this site is known to be critical to the properties of vinblastine [Borman et al., In *The Alkaloids*; Brossi, A., Suffness, M., Eds.; Academic: San Diego, 1990 37:133-144] and is found deeply embedded in the tubulin bound complex [Gigant et al., *Nature* 2005 435:519-522], the prior exploration of C20'-substituent effects has been limited to semi-synthetic O-acylation of the C20'-alcohol or its elimination and subsequent alkene reduction or superacid-catalyzed additions. [Miller et *J. Med. Chem.* 1977 20:409-413; Miller et al., Ger Patent 2753791 (*Chem. Abstr.* 1978 89:129778); Gerzon et al., Eur. Patent 55602 (*Chem. Abstr.* 1982 97:163310); Duflos et al., *Curr. Med. Chem. Anti-Cancer Agents* 2002 2:55-75.] These earlier reactions invariably led to substantial reductions in biological potency of the resulting derivative, albeit with examination of only a limited number of key analogues.

Consequently, in the course of the development of the Fe(III)/NaBH$_4$-mediated alkene functionalization reaction, its use was extended to the preparation of a series of key vinblastine analogues bearing alternative C20'-functionality. Those of initial interest included the C20'-azide and amine, both of which proved to be approximately 100-fold less potent than vinblastine (1) and 10-fold less potent than 20'-deoxyvinblastine (3).

However, acylation of the C20'-amine improved activity 10-fold and installation of the unsubstituted C20'-urea or thiourea provided compounds that nearly matched the potency of vinblastine itself. As will be seen hereinafter, a systematic exploration of C20'-amine, -urea, and -thiourea derivatives of vinblastine have not only provided C20'-urea-based analogues that substantially exceed the potency of vinblastine, but also exhibit good activity against a Pgp-over-expressing, vinblastine-resistant tumor cell line. Just as remarkably and in contrast to expectations based on the steric constraints of the tubulin binding site surrounding the vinblastine C20'-center as depicted in the x-ray co-crystal structure of a tubulin bound complex [Gigant et al., *Nature* 2005 435:519-522], large C20'-urea derivatives are accommodated, exhibiting potent functional activity in cell-based proliferation assays and effectively binding tubulin.

BRIEF SUMMARY OF THE INVENTION

The present invention contemplates a vinca alkaloid compound such as vinblastine, vincristine or vindesine that is substituted at the 20'-position with a urea or a thiourea group whose proximal nitrogen atom that is directly bonded to the 20'-position carbon atom is secondary and whose distal nitrogen is mono- or more preferably disubstituted; i.e., contains one or more preferably two substituents. These proximal and distal nitrogens are illustrated below in the partial structure of a contemplated compound showing atoms near the 20'-position and an urea derivative bonded to the 20'-carbon atom via the proximal urea nitrogen, with the distal urea nitrogen bonded to substituents R$^4$ and R$^5$.

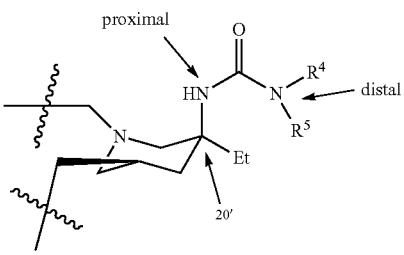

Except as discussed hereinafter, one of the distal nitrogen R$^4$ or R$^5$ substituents can be hydrido. Thus, at least one of R$^4$ and R$^5$ is other than hydrido (hydrogen), and more preferably both are other than hydrido. Preferably, R$^4$ and R$^5$ are independently a) a straight or branched chain hydrocarbyl group that has 1 to about 6 carbon atoms and is free of tertiary or quaternary carbon atoms, b) an aromatic or aliphatic carbocyclic or heterocyclic ring structure that contains one or two rings, up to twelve ring atoms, and up to four ring atoms that are independently nitrogen, oxygen or sulfur, c) an aralkyl or heteroaralkyl group containing 5- or 6-membered ring atoms and 1-3 carbons in the alkyl portion, or d) the two substituents bonded to the distal nitrogen atom (R$^4$ and R$^5$) together with that distal nitrogen atom form an aliphatic, heterocyclic or heteroaromatic ring structure containing a single ring or fused ring system having 5- to 10 ring atoms and can contains one or two additional hetero atoms that can independently be nitrogen, oxygen or sulfur. A ring structure of b) or c) or d) above can be optionally substituted with 1, 2 or 3 substituents selected from the group consisting of C$_1$-C$_6$-hydrocarbyl, C$_1$-C$_6$-hydrocarbyloxy, phenyl, halogen, perfluoro-C$_1$-C$_6$-hydrocarbyl, perfluoro-C$_1$-C$_6$-hydrocarbyloxy, nitro and mixtures thereof. An above contemplated 20'-substituted vinca alkaloid can also be further substituted with a fluoro group at the 10'-position of the molecule. A pharmaceutically acceptable salt of such a contemplated compound is also contemplated.

A preferred vinca alkaloid is a 20'-urea-substituted or thiourea-substituted vinblastine, vincristine or vindesine that can optionally also be substituted at the 10' position with a fluoro group rather than a hydrido as are illustrated by the structural Formula I shown below. These three compounds are structurally very similar and each

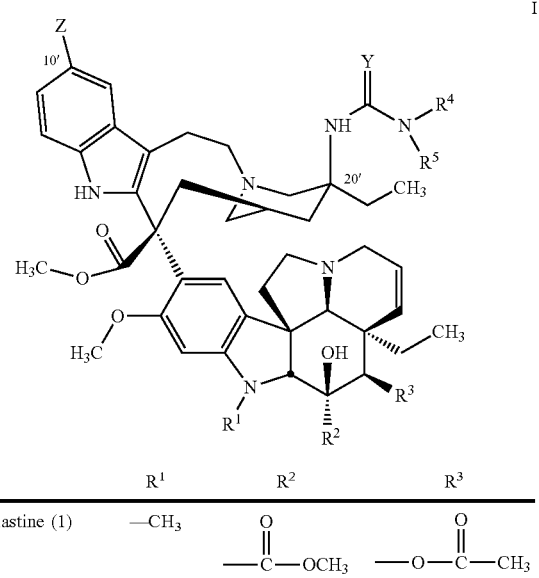

| | R$^1$ | R$^2$ | R$^3$ |
|---|---|---|---|
| Vinblastine (1) | —CH$_3$ | —C(O)—OCH$_3$ | —O—C(O)—CH$_3$ |

-continued

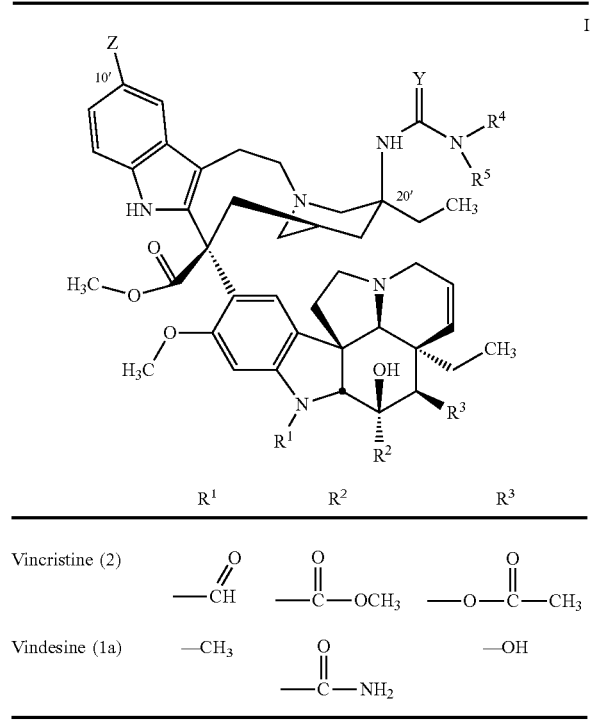

I

| | R¹ | R² | R³ |
|---|---|---|---|
| Vincristine (2) | —CH=O | —C(=O)—OCH₃ | —O—C(=O)—CH₃ |
| Vindesine (1a) | —CH₃ | —C(=O)—NH₂ | —OH | exhibits activity in anti-cancer therapies. In addition, as is shown in WO 2012/103700 A2, published Aug. 25, 2011, substitution of either vincristine or vinblastine at the 10'-position with a fluoro group provided compounds with almost identical activities in the anticancer areas assayed. Similarities in activity on substitution with other groups at other positions are also noted in the art among the vinca alkaloids and among these three particular alkaloid compounds.

Thus, in the above Formula I, Z is hydrido (H) or fluoro (F), Y is O or S, preferably O, and $R^4$ and $R^5$ are independently hydrido or a substituent as discussed below, except that $R^4$ and $R^5$ are both hydrido only when Z is F.

In one aspect, one or both of $R^4$ and $R^5$ is a straight or branched chain hydrocarbyl group other than a tertiary or quaternary hydrocarbyl group that has 1 to about 6 carbon atoms. When Z is H, at least one of $R^4$ and $R^5$ is other than hydrido, and more preferably both of $R^4$ and $R^5$ are other than hydrido. In another aspect of the invention, $R^4$ and $R^5$ can also be an aromatic or aliphatic carbocyclic or heterocyclic ring structure that contains one or two rings, up to twelve ring atoms, and up to four ring atoms that are independently nitrogen, oxygen or sulfur. $R^4$ and $R^5$ can be an aralkyl or heteroaralkyl group containing 5- or 6-membered ring atoms and 1-3 carbons in the alkyl portion in a third aspect. The two substituents on the distal nitrogen atom ($R^4$ and $R^5$) together with that nitrogen atom can form a single 5- or 6-membered ring or a fused ring system containing two rings, each of which can contain a 5- or 6-members and can also contain one or two additional hetero atoms that can independently be nitrogen, oxygen or sulfur in a fourth aspect of the invention.

Each of the before described rings or ring systems is optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof. An above contemplated 20'-substituted vinca alkaloid can also be further substituted with a fluoro substituent at the 10'-position of the molecule. A pharmaceutically acceptable salt of a preferred vinca alkaloid is also contemplated.

A pharmaceutical composition containing a cancer cell proliferation-inhibiting amount of a compound of a contemplated 20'-urea-substituted or thiourea-substituted vinca alkaloid such as vinblastine, vincristine and vindestine or a pharmaceutically acceptable salt thereof dissolved or dispersed in a physiologically (pharmaceutically) acceptable carrier or diluent is also contemplated.

A method of treating a diagnosed cancer is also contemplated. That treatment can be carried out in vitro or in vivo as within a mammalian subject, and comprises contacting the cancerous cells as by administering a therapeutically effective amount, e.g., a cancer cell proliferation-inhibiting amount, of a before-defined contemplated 20'-urea- or thiourea-substituted vinca alkaloid compound to a cancerous cell culture or to a mammalian subject, and preferably repeating that contacting (administration) over time to at least inhibit the growth (proliferation) of the cancer cells. The cancer cells so treated include those usually treated by an unsubstituted, parental vinca alkaloid compound such as vinblastine, vincristine or vindesine, and include hematologic cancer cells such as leukemia or lymphoma cells, as well as cells of carcinomas, sarcomas, melanomas, neuromas and the like.

The present invention has several benefits and advantages.

One benefit of the invention is that a preferred 20'-urea- or thiourea-substituted vinca alkaloid compound is about equal to about ten times more potent as a cytotoxic agent against a colorectal carcinoma cancer cell line than is a parental, unsubstituted vinca alkaloid such as vinblastine.

One advantage of the invention is that a preferred 20'-urea- or thiourea-substituted vinca alkaloid compound is about equal to about eighty times more potent against multiple drug resistant colorectal carcinoma cancer cell lines than is a parental, unsubstituted vinca alkaloid compound such as vinblastine.

Another benefit of the invention is that a contemplated 20'-urea- or thiourea-substituted vinca alkaloid compound is about equal to about ten times more potent as a cytotoxic agent against a leukemia cell line than is the parental, unsubstituted vinca alkaloid.

Another advantage of the invention is that a contemplated 20'-urea- or thiourea-substituted vinca alkaloid compound is relatively easy to synthesize.

Still further benefits and advantages will be apparent to those skilled in the art from the disclosures that follow.

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 6 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl and the like. Examples of suitable alkenyl radicals include ethenyl(vinyl), 2-propenyl, 3-propenyl, 1,4-pentadienyl, 1,4-butadienyl, 1-butenyl, 2-butenyl, 3-butenyl, hexenyl, hexadienyl and the like. Examples of alkynyl radicals include ethynyl, 2-propynyl, 3-propynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy groups and the like.

As a skilled worker will understand, a substituent that cannot exist such as a $C_1$ alkenyl group is not intended to be encompassed by the word "hydrocarbyl", although such substituents with two or more carbon atoms are intended.

The term "cyclohydrocarbyl" or "carbocyclic", alone or in combination, means a hydrocarbyl radical that contains 3 to about 8 carbon atoms, preferably about 3 to about 6 carbon atoms, and is cyclic. Examples of such cyclohydrocarbyl radicals include cyclopropyl, cyclobutyl, cyclopentenyl, cyclohexyl, cycloheptynyl and the like.

The term "aryl", alone or in combination, means a phenyl or naphthyl or other radical as recited hereinafter that optionally carries one two or three independently substituents selected from a $C_1$-$C_6$-hydrocarbyl group, $C_1$-$C_6$-hydrocarbyloxy group, a phenyl group, a perfluoro-$C_1$-$C_6$-hydrocarbyl group, a perfluoro-$C_1$-$C_6$-hydrocarbyloxy group, a halogen (fluoro, chloro or bromo) group, a nitro group and the like, such as phenyl, 4-tolyl, 3-chloro-4-ethoxyphenyl, 4-(tert-butoxy)phenyl, 4-fluorophenyl, 4-chlorophenyl, 2,3-dimethoxyphenyl, 3,4,5-trimethoxyphenyl, 4-trifluoromethylphenyl, and the like.

The heterocyclyl(heterocyclo) is a 5- or 6-membered ring that contains 1 to 4 hetero atoms (non-carbons) in the ring that independently are nitrogen, oxygen or sulfur atoms in a saturated or partially unsaturated ring that is optionally substituted on one or more ring carbon atoms by a halogen, hydrocarbyl, hydrocarbyloxy, oxo group, and the like, and/ or on a secondary ring nitrogen atom (i.e., —NH—) by a hydrocarbyl group, wherein a hydrocarbyl or hydrocarbyloxy group contains 1 to about 6 carbon atoms, and preferably 1 to about 4 carbon atoms. Examples of such heterocyclyl groups are pyrrolidinyl, piperidinyl, piperazinyl, di- and tetrahydropyridyl, 4-($C_1$-$C_6$-hydrocarbyl)-piperidinyl, 4-phenylpiperidinyl, quinolinyl, isoquinolyl, indolinyl, tetrahydroindolinyl, isoindolinyl, tetrahydroisoindolinyl, morpholinyl, thiomorpholinyl, oxathiazolyl, 1,2,3-triazolyl, 1,2,4-triazolyl, pyrazolyl, 1,2,4-oxadiazinyl and azepinyl groups and the like.

A "heteroaryl" group is an aromatic heterocyclic ring that preferably contains one, or two, or three or four atoms in the ring other than carbon. Those heteroatoms can independently be nitrogen, sulfur or oxygen. A heteroaryl group can contain a single 5- or 6-membered ring or a fused ring system having two 6-membered rings or a 5- and a 6-membered ring. Exemplary heteroaryl groups include 6-membered ring substituents such as pyridyl, pyrazyl, pyrimidinyl, and pyridazinyl; 5-membered ring substituents such as 1,3, 5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl, tetrahydroisoquinolinyl, tetrahydroisoindolinyl, and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

The term "halogen" means fluorine, chlorine or bromine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1, 1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl. A halohydrocarbyloxy substituent is a halogenated ether such as a trifluoromethoxy group and the like.

DETAILED DESCRIPTION OF THE INVENTION

The present invention contemplates a 20'-urea- or thiourea-substituted vinca alkaloid compound or pharmaceutically acceptable salt of such a compound. More particularly, a contemplated vinca alkaloid compound that is substituted at the 20'-position with a urea or thiourea group whose proximal nitrogen atom that is directly bonded to the 20' carbon atom is secondary (has one hydrogen atom bonded to it) and whose distal nitrogen is contains one, and more preferably contains two non-hydrido substituents (the $R^4$ and $R^5$ groups in the formula below) when the vinca alkaloid compound does not contain a 10'-fluoro group. A preferred vinca alkaloid compound is a 20'-substituted vinblastine, vincristine or vindesine that can optionally be further substituted at the 10'-position with a fluoro group and corresponds in structure to Formula I below:

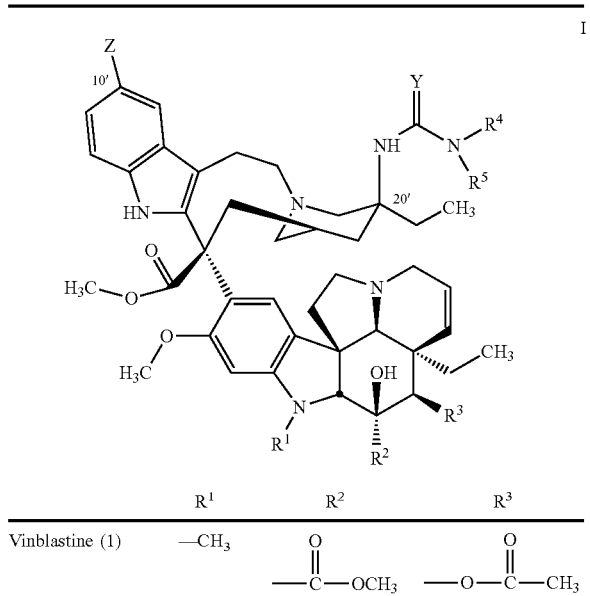

-continued

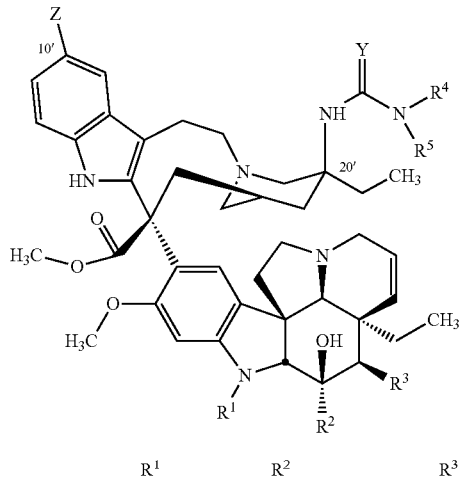

| | $R^1$ | $R^2$ | $R^3$ |
|---|---|---|---|
| Vincristine (2) | —CH(=O) | —C(=O)—OCH$_3$ | —O—C(=O)—CH$_3$ |
| Vindesine (1a) | —CH$_3$ | —C(=O)—NH$_2$ | —OH | where Z is H or F, and $R^4$ and $R^5$ are discussed hereinafter.

The $R^4$ and $R^5$ substituents are independently selected from the group consisting of hydrido, a) a straight or branched chain or cyclic hydrocarbyl group that has 1-6 carbon atoms, and preferably 2-6 carbon atoms, that is free of tertiary or quaternary carbon atoms, b) an aromatic or aliphatic carbocyclic or heterocyclic ring structure that contains one or two rings, up to twelve ring atoms, and up to four ring atoms that are independently nitrogen, oxygen or sulfur. A third substituent, c) is an aralkyl or heteroaralkyl group containing 5 or 6 ring atoms of which up to three ring atoms can independently be nitrogen, oxygen or sulfur and contains 1-3 carbons in the alkyl portion. Alternatively, d) two substituents bonded to the distal nitrogen atom together with that distal nitrogen atom form a single 5- or 6-membered aliphatic or aromatic ring or a fused ring system containing two rings each of which contains 5- or b-ring atoms. At least one of the $R^4$ and $R^5$ substituents of a)-d) above is other than hydrido, and more preferably, both $R^4$ and $R^5$ substituents are other that hydrido when Z is H. When Z is F, both of $R^4$ and $R^5$ can be H, but it is preferred that only one be H and more preferred that both of $R^4$ and $R^5$ be other than H.

The single or fused ring system of d) can contain one or two additional hetero atoms that can independently be nitrogen, oxygen or sulfur. Each of the rings or ring systems of b), c) and d) above can optionally be substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof.

Examining the preferred one or more preferred two distal nitrogen atom substituents ($R^4$ and $R^5$ groups) more closely, both of $R^4$ and $R^5$ can be hydrido only when Z is F, but preferably, at least one of $R^4$ and $R^5$ is other than hydrido, and more preferably both of $R^4$ and $R^5$ are other than hydrido. One preferred $R^4$ and/or $R^5$ substituent is a straight or branched chain hydrocarbyl group that has 1-6 carbon atoms, and preferably 2-6 carbon atoms, that is free of tertiary or quaternary carbon atoms. Exemplary hydrocarbyl substituent groups have been generally discussed previously. This hydrocarbyl group excludes those substituents that contain a tertiary carbon atom as in a t-butyl group [(CH$_3$)$_3$C—] or a quaternary carbon as is present in a neo-pentyl group [(CH$_3$)$_3$CH$_2$—].

A second group of distal nitrogen substituents ($R^4$ and/or $R^5$) is an aromatic or aliphatic carbocyclic or heterocyclic ring structure that contains one or two rings, up to twelve ring atoms, and up to four ring atoms that are independently nitrogen, oxygen or sulfur. That ring structure is optionally substituted with 1, 2 or 3 substituents (ring substituents) that are themselves selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof. Illustrative ring structures include phenyl, biphenyl, naphthyl, cyclopropyl, cyclopentyl, cyclohexyl, cycloheptyl, cyclodecyl, pyridyl, furanyl, purinyl, isoquinolinyl, tetrahydroisoindanyl and the like that are discussed hereinbefore.

A contemplated aromatic or aliphatic carbocyclic or heterocyclic ring structure $R^4$ and/or $R^5$ substituent can contain 1-3 of its own substituents but preferably contains only one such as a halogen like chloro or fluoro, a $C_1$-$C_6$-hydrocarbyl group such as methyl, a $C_1$-$C_6$-hydrocarbyloxy group such as methoxy, a perfluoro-$C_1$-$C_6$-hydrocarbyl group such as trifluoromethyl or a perfluoro-$C_1$-$C_6$-hydrocarbyloxy group such as pentafluoroethoxy. When more than one substituent is present on a ring structure substituent, those multiple substituents need not be the same group.

One preferred nitrogen substituent contains one ring that contains 3-6 carbon atoms in the ring. Another preferred substituent is an aromatic ring structure that contains one or two rings. One preferred aromatic ring contains one substituent.

Another contemplated group of distal nitrogen atom $R^4$ and/or $R^5$ substituents is an aralkyl or heteroaralkyl group containing 5 or 6 ring atoms of which up to three ring atoms can independently be nitrogen, oxygen or sulfur and 1-3 carbons in the alkyl portion. The aromatic ring portion of a contemplated ring structure is optionally substituted with 1, 2 or 3 substituents that are selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, as are discussed above. Zero or one ring substituent other than hydrogen is preferred.

Illustrative 5- or 6-membered aromatic and heteroaromatic ring substituents were also discussed previously. The alkyl portion of an aralkyl or heteroaralkyl group can contain 1 to 3 carbon atoms. Illustrative non-ring-substituted aralkyl groups include benzyl and phenethyl groups, whereas illustrative heteroaralkyl groups include methylpyridyl and ethylimidazolyl.

A distal urea nitrogen atom can also form a ring structure together with the two $R^4$ and $R^5$ substituent groups. That nitrogen-containing ring structure can contain a single 5- or 6-membered ring or contain a fused two ring structure in which the rings are both 5-membered, or both 6-membered, or in which one ring is 5-membered and the other is 6-membered. A contemplated ring structure can also contain one or two additional hetero atoms (non-carbon atoms) in the ring(s) that can be independently nitrogen, oxygen or sulfur. This nitrogen-containing ring is preferably a 6-membered ring or a 5-/6-membered fused ring system. 20'-Urea- or thiourea-substituted vinblastine compounds are illustrated hereinafter that contain distal nitrogen atoms that are present in 5-, 6-, 6/6- and 5/6-membered rings.

These nitrogen-containing rings can be aromatic as in the case of an 1-imidazyl, 1-pyrazolyl, 1-(1,2,4-triazolyl), 2-o-isoxazinyl or a 2-(1,3,2-dioxazolyl) group, but are more usually aliphatic such as 1-piperidinyl, 1-pyrrolidinyl, 1-piperazinyl, 1-morpholinyl, 1-thiomorpholinyl, isoquinolinyl, tetrahydroisoindolinyl and the like. It is noted that a —NR$^4$R$^5$ cyclic substituent that contains a free hydrogen atom such as that of a secondary nitrogen (—NH—) present on the 4-position nitrogen of piperazine ring are blocked as with a t-Boc, F-moc, acetyl, $C_1$-$C_6$-hydrocarbyl such as methyl, or other group during synthesis and thereafter because of the reactivity with an isocyanate or isothiocyanate reagent.

A urea nitrogen atom-containing ring structure is optionally substituted with 1, 2 or 3 substituents that are selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof.

A phenyl substituent bonded to a piperidinyl group or the aromatic portion of a ring structure formed by a —$NR^4R^5$ cyclic structure can contain 1-3 substituents independently selected from the group consisting $C_1$-$C_6$-hydrocarbyl, $C_1$-$C_6$-hydrocarbyloxy, perfluoro-$C_1$-$C_6$-hydrocarbyl, perfluoro-$C_1$-$C_6$-hydrocarbyloxy, halogen (fluoro, chloro or bromo) and nitro, Another aspect of the invention is a doubly substituted vinca alkaloid compound. This compound contains a 20'-urea or thiourea group as discussed above, and also contains an added fluoro (F) substituent at the 10'-position of the molecule. The preparation of different fluoroinated vinca alkaloids was discussed in Va et al., *J Am Chem Soc* 2010 132:8489-8495 and in WO 2011/103007 published on 25 Aug. 2011, but that synthesis can also be used herein. As is seen from the data that follows, the presence of both the 20'-urea substitution and the 10'-fluoro substitution in a vinblastine molecule provided growth inhibitory activity against each of the cancer cell lines examined that was greater than the inhibitory activity of either substitution alone.

Pharmaceutical Composition and Methods

A contemplated 20'-urea- or thiourea-substituted vinca alkaloid compound can also be used in the manufacture of a medicament (pharmaceutical composition) that is useful at least for inhibiting the proliferation (growth) of hematologic cancer cells such as leukemia or lymphoma cells, as well as cells of carcinomas, sarcomas, melanomas, neuromas and the like. A contemplated compound, medicament or pharmaceutical composition containing the same inhibits that growth by contacting those cancerous cells in vitro, or in vivo as in a subject in need thereof, as is a parent compound. When so used, pharmaceutically acceptable salts, buffers and the like are present that collectively are referred to as pharmaceutically acceptable diluents as compared to those that can be present in a composition that is not intended for pharmaceutical use, as in an in vitro assay.

A compound of the invention can be provided for use by itself, or as a pharmaceutically acceptable salt. The contemplated compounds are amines. Parental vinblastine has reported pKa values of 5.4 and 7.4, whereas vincristine has reported pKa values of 6.04 and 7.67. [*The Merck Index*, 13$^{th}$ ed. Merck & Co., Whitehouse Station, N.J., 2001, pages 1778-1779.] Both compounds are sold commercially as their sulfate salts. Vindesine is reported to have pka values of 6.04 and 7.67 [*The Merck Index*, 12$^{th}$ ed., Merck and Co., Whitehouse Station, N.J., 1996, page 1704]. Vindesine is also commercially available as the sulfate salt.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vitro assay studies at nanomolar to micromolar amounts. When used in an assay such as an in vitro assay, a contemplated compound is present in the composition in an amount that is sufficient to provide a concentration of about 0.5 nM to about 1000 nM, preferably about 1 nM to about 50 nM to a contact cells to be assayed.

A contemplated pharmaceutical composition contains a cancerous cell proliferation-inhibiting amount of a contemplated 20'-urea- or thiourea-substituted vinca alkaloid compound or a pharmaceutically acceptable salt thereof dissolved or dispersed in a physiologically (pharmaceutically) acceptable carrier. That amount is typically about the same amount to a little less than the amount of a parental vinca alkaloid used to treat the same cancer. Such a composition can be administered to mammalian cells in vitro as in a cell culture to contact those cells, or the cells can be contacted in vivo as in a living, host mammal in need.

More usually, anti-neoplastic drugs such as a 20'-substituted vinca alkaloid contemplated here are administered parenterally in vivo in a weight amount per square meter of the recipient's body surface area (bsa). For adults, this amount is typically about 1 to about 20 mg/m$^2$ bsa, and about one-half those amounts for children, with an amount being chosen so that the maximal amount does not cause leukopenia. Children weighing about 10 kg or less are typically dosed at about 0.05 mg/kg.

For example, vinblastine sulfate is typically administered to adults at 3.7 mg/m$^2$ bsa for the first dose, 5.5 mg/m$^2$ bsa for the second weekly dose, 7.4 mg/m$^2$ bsa for the third weekly dose, 9.25 mg/m$^2$ bsa for the fourth weekly dose and 11.1 mg/m$^2$ bsa for the fifth weekly dose. Dosages typically do not exceed 18.5 mg/m$^2$ bsa, and should not be increased if the white-cell count falls to approximately 3000 cells/mm$^3$. Usual dosages for adults are about 5.5 to 7.4 mg/m$^2$ bsa. Dosages of a contemplated 20'-position urea- or thiourea-substituted vinca alkaloid compound or its pharmaceutically acceptable salt typically do not exceed those of the parent compound and can be less.

A contemplated composition is typically administered in vivo to a subject in need thereof a plurality of times within one month, such as weekly, and can be administered over a period of several months to several years. More usually, a contemplated composition is administered a plurality of times over a course of treatment.

In usual practice, a contemplated 20'-urea- or thiourea-substituted vinca alkaloid compound is administered to treat the same disease state in the same amount and at the same intervals as is a parental, 20'-hydroxy-vinca alkaloid. A contemplated 20'-urea- or thiourea-substituted vinca alkaloid can be utilized as a first course of treatment, and is preferably administered if there is relapse after a first or later course of treatment, particularly where multiple drug resistance is shown or suspected (indicated).

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous (which is most preferred), intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a contemplated compound in a solid dosage form is as discussed previously, an amount sufficient to provide a concentration of about 0.5 nM to about 1000 nM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a 20'-urea- or thiourea-substituted vinca alkaloid active component or sterile solution of the active component in solvents comprising water, ethanol, or propylene glycol are examples of liquid compositions suitable for parenteral administration. In some aspects, a contemplated 20'-urea- or thiourea-substituted vinca alkaloid is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain the water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated 20'-urea- or thiourea-substituted vinca alkaloid is administered with one or more other anti-neoplastic compounds. Such joint therapy is well known in the art, with other drugs such as cisplatin, 5-fluorouracil and the like being co-administered. That co-administration is usually physically separate administrations of each compound that are timed so that the two or more active agents can act in concert.

Results and Discussion

Chemistry.

The targeted vinblastine C20'-urea and -thiourea analogues were prepared by two methods (Scheme 1). The first method (Method 1) involved Scheme 1

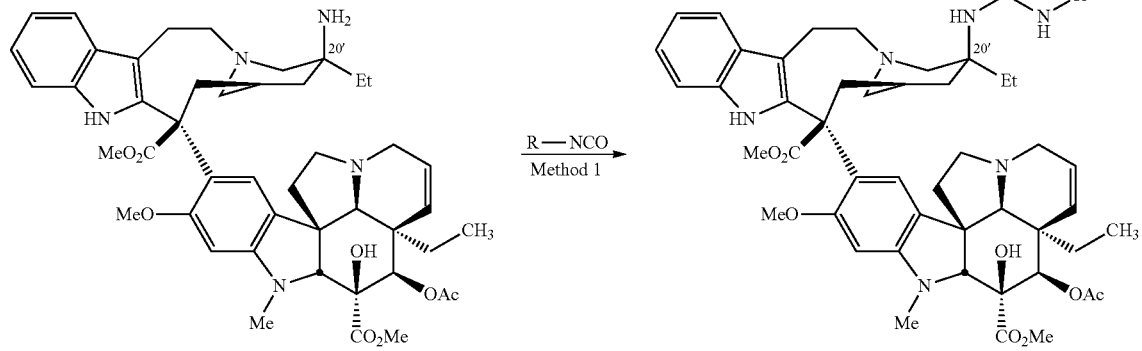

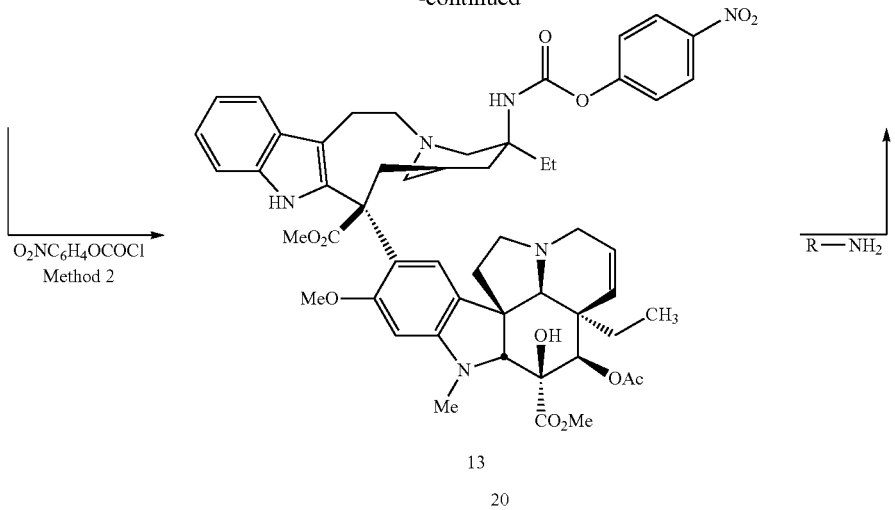

treating the recently accessible 20'-aminovinblastine (7) [Leggans et al., *Org. Lett.* 2012, 14:1428-1431] with available isocyanates to provide the corresponding ureas. In the instances when the isocyanates were not readily available, Method 2 was used. This method entailed treating 20'-aminovinblastine (7) with p-nitrophenyl-chloroformate to provide the activated carbamate 13, which was then treated with a series of amines to provide the additional C20'-urea analogues.

The vinblastine C20'-thiourea analogues were prepared also using two complementary methods (Scheme 2). Thus, treatment of 20'-aminovinblastine (7) with a small series of commercially available Scheme 2

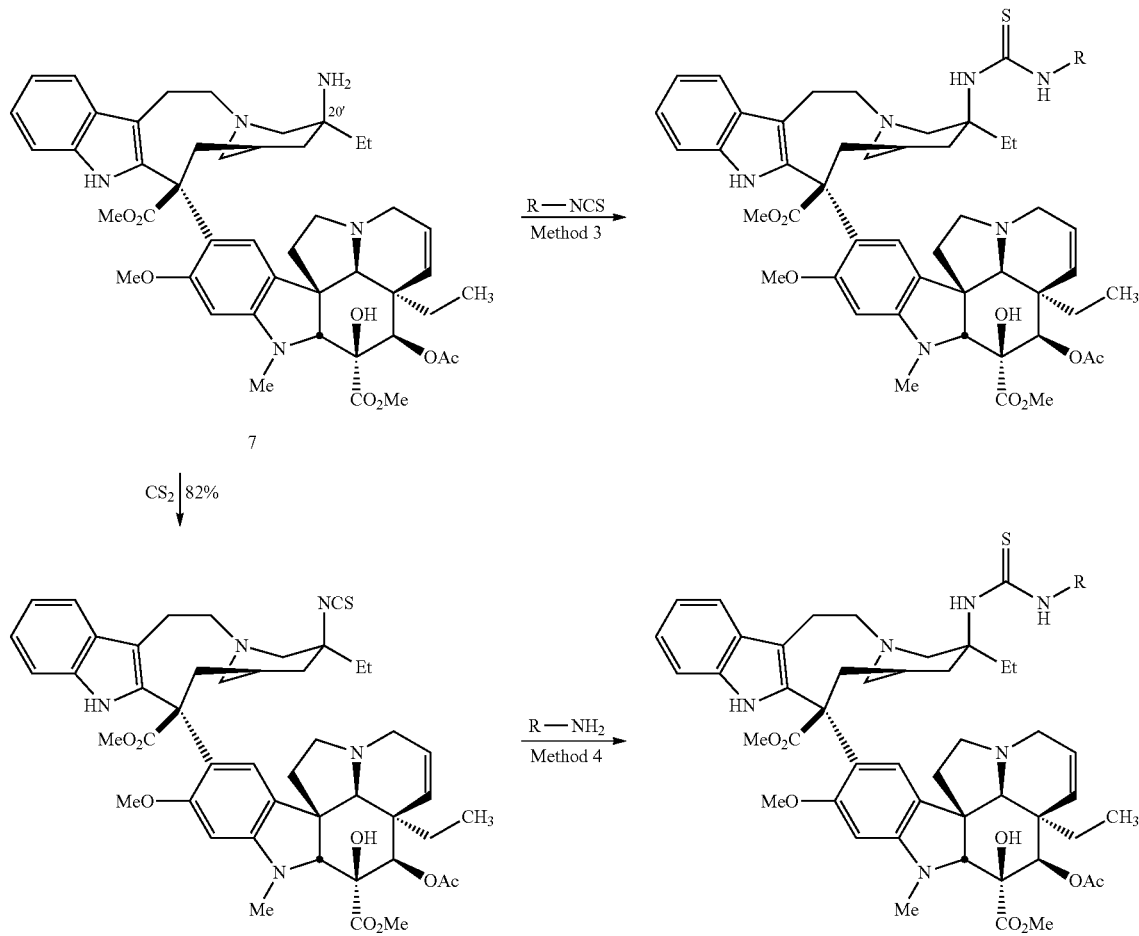

isothiocyanates (Method 3) versus isocyanates provided the corresponding C20'-thiourea analogues. Alternatively, treatment of 20'-isothiocyano-vinblastine (5) [Leggans et al., *Org. Lett.* 2012 14:1428-1431], made from the reaction of 20'-aminovinblastine (7) and carbon disulfide (82%) or that is available upon direct Fe(III)/NaBH$_4$-mediated functionalization of anhydrovinblastine (KSCN) [Leggans et al., *Org. Lett.* 2012 14:1428-1431] with available amines (Method 4) also provided a set of C20'-thiourea vinblastine analogues.

A series of N,N-disubstituted C20'-urea and -thiourea vinblastine analogues were also prepared using Methods 2 and 4 and commercially available N,N-disubstituted amines. Additionally, the carbamate analogue 45 was synthesized for direct comparison with what proved to be the potent C20'-urea and -thiourea derivatives. Thus, vinblastine (1) was treated with the N,N-dimethylcarbamyl chloride to provide the C20'-carbamate 45 (below).

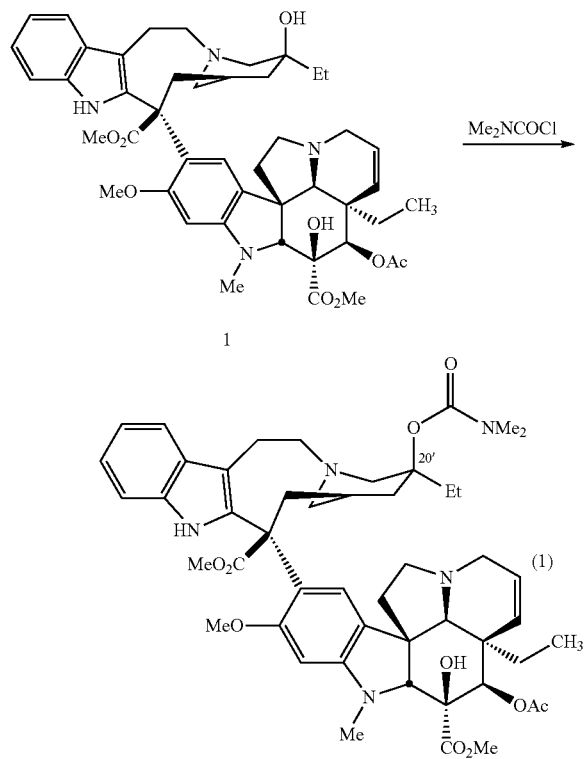

Biological Activity.

The C20'-substituted vinblastine analogues were examined for cell growth inhibitory activity against the HCT116 (human colon cancer), and HCT116/VM46 (resistant human colon cancer) tumor cell lines, the latter of which exhibits resistance (100-fold) to vinblastine through overexpression of Pgp. [Lampidis et al., *Biochemistry* 1997 36:2679-2685; Perego et al., *Cancer Res.* 2001 61:6034-6037.] As reported [Leggans et al., *Org. Lett.* 2012 14:1428-1431], the unsubstituted urea 11 on which the studies are based approached but did not match the potency of vinblastine. The results of the examination of the systematically varied monosubstituted C20'-urea derivatives prepared herein are summarized in the Table below alongside those of vinblastine (1) and the unsubstituted urea (11) of Leggans et al., *Org. Lett.* 2012 14:1428-1431.

The cell growth inhibition activity against the L1210 (mouse leukemia) cancerous cell line was also measured and the results were qualitatively and quantitatively (IC$_{50}$) nearly identical to those observed with the HCT116 cancerous carcinoma cell line in that IC$_{50}$ values were obtained for the urea derivatives that matched or exceeded the activity of vinblastine itself. Results are shown below.

|  | IC$_{50}$ (nM) | | |
| --- | --- | --- | --- |
| Compound | L1210 | HCT116 | HCT116/VM46 |
| Vinblastine (1) | 6.0 | 6.8 | 600 |
| R = H (11) | 40 | 7.5 | 4400 |
| Alkyl | | | |
| R = methyl (14) | 5.7 | 0.82 | 530 |
| R = ethyl (15) | 2.1 | 0.73 | 90 |
| R = n-propyl (16) | 6.0 | 2.7 | 221 |
| R = i-propyl (17) | 5.5 | 5.7 | 430 |
| R = cyclopropyl (18) | 3.9 | 0.73 | 85 |
| R = n-butyl (19) | 5.7 | 4.6 | 270 |
| R = t-butyl (20) | 40 | 20 | 670 |
| R = cyclohexyl (21) | 5.8 | 5.4 | 450 |
| R = 2-hydroxyethyl (22) | 48 | 8.8 | >1000 |
| Aryl | | | |
| R = C$_6$H$_5$ (23) | 6.5 | 5.1 | 390 |
| R = p-C$_6$H$_4$F (24) | 5.7 | 3.9 | 400 |
| R = p-C$_6$H$_4$Cl (25) | 6.2 | 6.7 | 590 |
| R = p-C$_6$H$_4$CH$_3$ (26) | 4.5 | 4.8 | 330 |
| R = p-C$_6$H$_4$CF$_3$ (27) | 7.3 | 7.1 | 610 |
| R = p-C$_6$H$_4$OCH$_3$ (28) | 4.9 | 2.0 | 230 |
| R = m-C$_6$H$_4$OCH$_3$ (29) | 5.4 | 0.77 | 80 |
| R = o-C$_6$H$_4$OCH$_3$ (30) | 4.8 | 0.77 | 65 |
| R = CH$_2$C$_6$H$_5$ (31) | 6.4 | 7.3 | 740 |
| R = CH$_2$CH$_2$C$_6$H$_5$ (32) | 6.3 | 6.3 | 590 |
| R = CH$_2$(2-pyridyl) (33) | 24 | 5.6 | 670 |
| R = CH$_2$(2-furyl) (34) | 5.4 | 5.1 | 530 |

Terminal N-alkyl substituents were not only well tolerated, but provided significant enhancements in activity, improving on the potency of 11 and providing derivatives that substantially surpass that of vinblastine itself. Most notable of these are the urea derivatives 14-18, bearing small N-alkyl substituents. Some of those compounds exhibited IC$_{50}$ values of 700-800 pM against HCT116, improving activity against HCT116 about 10-fold relative to 11, and substantially surpassing the potency of vinblastine itself (about 10-fold).

Even the larger N-alkyl derivatives 19 and 21 matched or slightly surpassed the activity of vinblastine and only 20, bearing the large t-butyl substituent, experienced a small, but surprisingly modest loss in activity given expectations. Introduction of a polar group that can serve as either a H-bond donor or acceptor on the alkyl substituent in 22 maintained the activity observed with other small alkyl substituents in the HCT116 cell line; however, it had a deleterious effect in the potency against the resistant cell line (IC$_{50}$>1000 nM, HCT116/VM46), similar to that seen in the parent urea 11.

The examination of the monosubstituted C20'-urea derivatives bearing N-aryl substituents (23-30) proved even more unexpected. All exhibited cell growth inhibitory activity at levels exceeding the parent urea 11, matching or surpassing the potency of vinblastine itself. Electron-withdrawing or electron-donating substituents on the parent N-phenyl urea 23 are well tolerated.

Although no strongly polar substituents were examined, it is notable that the p-methoxy substituent proved to be among the best of the p-substituents. As a result, the impact of a m- and o-methoxy phenyl substituent was also examined. Significantly, 29 and 30 bearing N-(m-methoxyphenyl) and N-(o-methoxyphenyl) urea substituents respectively, exhibited exceptional activity, substantially exceeding the potency of vinblastine nearly 10-fold ($IC_{50}$ 770 pM vs 6.8 nM, HCT116) and displaying uniquely potent activity against the vinblastine-resistant HCT116 cell line ($IC_{50}$=80 and 65 nM, HCT116/VM46). This activity along with that of 15 and 18 represents a 10-fold improvement over vinblastine.

Placement of a one or two methylene spacer between the phenyl ring and urea nitrogen (31 and 32) maintained activity with both derivatives matching the activity of both 23 and vinblastine itself. Replacement of the phenyl ring in 31 with a heteroaromatic ring (furan or pyridine) provided 33 and 34, which displayed comparable activity to the parent 31, matching or slightly exceeding the potency of vinblastine.

All these observations are unexpected given the apparent steric constraints of the tubulin binding site surrounding the vinblastine C20'-center observed in the x-ray crystal structure of a tubulin bound complex. [Gigant et al., *Nature* 2005 435:519-522.] To further probe just how much space may be available to a C20'-derivative, the rigid N-biphenyl urea 35 was prepared and examined. Remarkably, it displayed cell growth inhibitory activity at a level indistinguishable from vinblastine, below.

| Compound | HCT116 | HCT116/VM46 |
|---|---|---|
| | $IC_{50}$ (nM) | |
| 1 | 6.8 | 600 |
| 35 | 6.9 | 470 |

This result indicates that sterically demanding modifications to such C20'-urea derivatives are likely even beyond those probed herein. As a result and in addition to improvements in potency, this may be a superb site for modulating the physical and chemical properties of the drug that impact additional features including Pgp efflux [Hitchcock, *J. Med. Chem.* 2012 55:4877-4895], in vivo drug distribution, selective cellular uptake, and metabolism.

A series of thiourea derivatives was also examined as shown below. Although the unsubstituted thiourea derivative 12 approached the activity of the corresponding urea 11 in the original studies ($IC_{50}$=7.7 vs 7.5 nM, HCT116), the monosubstituted N-alkyl or N-aryl derivatives 36 and 37 proved to be 3- to 4-fold less active than the corresponding ureas 21 and 23 (HCT116). However, it is notable that the activity difference between sensitive and vinblastine-resistant cell lines diminished in this thiourea series (15- to 25-fold vs 100-fold), suggesting they may be transported by Pgp somewhat less effectively. [Hitchcock, *J. Med. Chem.* 2012 55:4877-4895]

| Compound | HCT116 | HCT116/VM46 |
|---|---|---|
| | $IC_{50}$ (nM) | |
| Vinblastine | 6.8 | 600 |
| R = H (12) | 7.7 | 2000 |
| R = $C_6H_{11}$ (36) | 20 | 520 |
| R = $C_6H_6$ (37) | 40 | 650 |
| R = $CH_2CH_2$(4-$FC_6H_4$) (38) | 60 | 750 |

A small, but important series of N,N-disubstituted ureas and thioureas was also examined in order to establish whether the terminal urea nitrogen could be fully substituted or whether the derivatives require or benefit from the presence of an N—H H-bond donor, below. Remarkably, all the N,N-disubstituted ureas exhibited potent cell growth inhibitory activity matching or surpassing the activity of vinblastine and indicating that a terminal H-bond donor site is not important to their functional activity.

However, both 39 and 40 were less active than the corresponding monosubstituted urea derivatives 14 and 15. Ureas with cyclic substituents on the terminal nitrogen, 41 and 42, exhibited a similar potency to the acyclic derivatives 39 and 40. An analogous observation was made with the N,N-dimethyl thiourea derivative 43, which approached the potency of vinblastine but exhibited activity slightly lower than the corresponding N,N-dimethyl urea 38.

Interestingly, and like the thiourea derivatives 36 and 37, Compound 43 and especially the urea derivatives 39 and 42 exhibited a diminished activity difference between sensitive and vinblastine-resistant HCT116 cell lines (10-fold vs 100-fold). Comparison of the N,N-dimethyl urea or thiourea 39 and 43 with the N,N-dimethylcarbamate 44 (>1000-fold less active) clearly illustrates the distinction and importance of the C20'-amine versus C20'-alcohol functionalization, suggesting the H-donor capabilities of the former may be important.

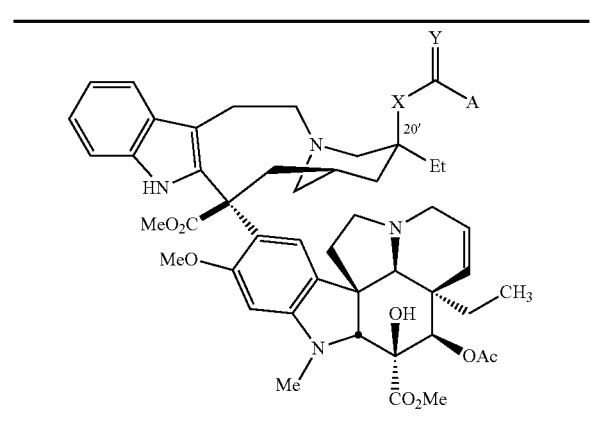

X = O, NH
Y = O, S

| Compound | IC50 (nM)[a] | | |
|---|---|---|---|
| | L1210 | HCT116 | HCT116/VM46 |
| Vinblastine (1) | 6.0 | 6.8 | 600 |
| X = NH, Y = O | | | |
| A = NH₂ (11) | 40 | 7.5 | 4400 |
| A = N(CH₃)₂ (39) | 5.9 | 2.8 | 80 |
| A = N(CH₂CH₃)₂ (40) | ND | 6.7 | 450 |
| A = N–morpholine (41) | 5.3 | 4.5 | 360 |
| A = N–piperidine (42) | 5.5 | 3.9 | 50 |
| A = N–pyrrolidine (52) | 0.7 | 0.72 | 50 |
| A = O–C₆H₄–NO₂ (13) | ND | 55 | ND |
| A = N–thiomorpholine (53) | 2.1 | 0.88 | 50 |
| A = N–N(CH₃)piperazine (54) | 7.7 | 3.4 | 710 |
| A = N–tetrahydropyridine (55) | 0.52 | 0.52 | 8.4 |

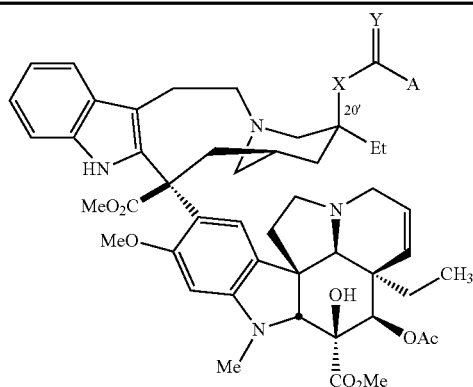

X = O, NH
Y = O, S

| Compound | IC50 (nM)[a] | | |
|---|---|---|---|
| | L1210 | HCT116 | HCT116/VM46 |
| A = N–(4-phenyl)piperidine (56) | 5.3 | 3.1 | 55 |
| A = tetrahydroisoquinoline (57) | 0.62 | 0.56 | 8.7 |
| A = isoindoline (58) | 0.51 | 0.60 | 7.5 |
| A = 5-OMe-isoindoline (59) | 0.61 | 0.69 | 8.7 |
| X = NH, Y = S | | | |
| A = NH₂ (12) | ND | 7.7 | 2000 |
| A = N(CH₃)₂ (43) | ND | 8.7 | 250 |
| X = O, Y = O | | | |
| A = N(CH₃)₂ (44) | ND | 4700 | 9100 |

[a]L1210 (murine leukemia cell line).
HCT116 (human colon cancer cell line).
HCT116/VM46 (resistant human colon cancer cell line, Pgp over-expression).
Avg IC$_{50}$ (4-16 determinations, SD = ±10%).
ND = Not Done.

Cell growth inhibition by disubstituted C20' urea analogs was systematically probed, incorporating cyclic amines as the terminal nitrogen (below). Compounds 42 and 53-54 exhibited little or no change in the activity against the sensitive HCT116 cell line, but show a clear trend against the resistant HCT116/VM46 cell line with the incorporation of a polar atom in the six-membered ring having a pronounced negative effect on the activity (C=S>O>NMe). After observing this trend, analogs were prepared incorporating additional non-polar functionality on the terminal cyclic amine (Compounds 55-59).

C20'-Urea vinblastine analogs in which the terminal nitrogen is allylic (Compound 55) or benzylic (Compounds 57-59) provided a further enhancement in the activity of approximately 10-fold relative to vinblastine and where the resulting activity against the resistant HCT116/VM46 is 80-fold better than vinblastine and 8-fold better than the saturated piperidine-based urea 42. Incorporation of a six-membered cyclic amine with a hydrophobic phenyl substituent that was not benzylic (Compound 55) to the urea nitrogen did not provide the enhanced activity in the HCT116/VM46 cell line observed with the unsaturated piperidine Compound 55 or fused phenyl ring analogs Compounds 57-59. This result suggests that an electronic effect is contributing to the enhanced activity and that it may not simply be the additional van der Waal interactions derived from an added hydrophobic aromatic ring. Addition of a methoxy group to the potent isoindoline (Compound 59) did not further impact the cell growth activity.

Significant in these observations is not only the exceptional activity of the new derivatives, but their reduced differential in activity against the sensitive and resistant tumor cell line (about 13-16-fold versus about 90-fold for Compound 1). Presumably, this indicates that the new derivatives are not as effective substrates for Pgp efflux as vinblastine itself, whereas the more polar analogs Compounds 41 and 54 and especially the unsubstituted urea Compound 11 are effective substrates.

Clearly, the C20'-position within vinblastine represents a key site amenable to functionalization capable of simultaneously enhancing potency and presumably decreasing relative Pgp transport central to clinical resistance.

Although less pronounced, but as detailed in the initial report [Leggans et al., Org. Lett. 2012 14:1428-1431] the amide 9 and methyl carbamate 10 were found to be more than 10-fold less active than the urea 11, further highlighting a unique role the urea terminal nitrogen plays in potentiating the activity. The importance of the C20'-amine versus alcohol functionalization and distinctions between urea/thiourea versus carbamate/amide derivatives is illustrated in the Table below.

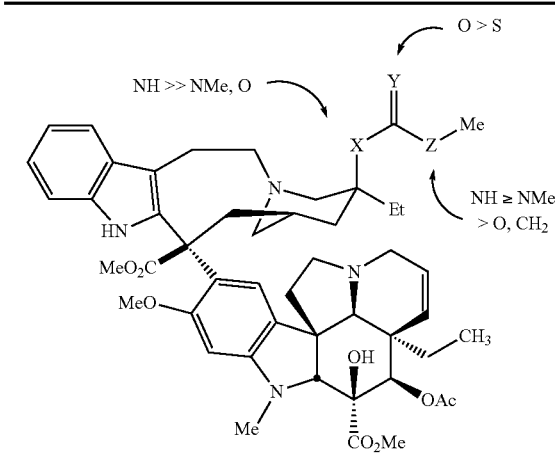

| Compound | X | Y | Z | IC$_{50}$ (nM) HCT116 |
|---|---|---|---|---|
| 10 | NH | O | O | 75* |
| 9 | NH | O | — | 90* |
| 44 | O | O | NMe | 4700 |

*Leggans et al., Org. Lett. 2012 14:1428-1431.

As a result and given the size of substituents tolerated, even the intermediate p-nitrophenyl-carbamate 13 used to prepare the ureas herein was tested and proved to be a surprisingly effective agent (IC$_{50}$=55 nM, HCT116), matching the activity of the methyl carbamate 10.

Two additional C20'-amines (45 and 46) were prepared by reductive amination (H$_2$CO (5 equiv), NaBH$_3$CN (20 equiv), THF, 4 hours, 32% (45) NHMe, 33% (46) NMe$_2$) of 20'-aminovinblastine (7) in order to establish the generality of the observations made with the unsubstituted primary amine 7 itself, and the results are shown below. Although the C20'-methylamine proved more potent than 7, it was still 10-fold less active than vinblastine and the C20'-dimethylamine derivative 46 was the least active of the C20'-amines examined, suggesting the importance of a H-bond donor with regard to biological activity.

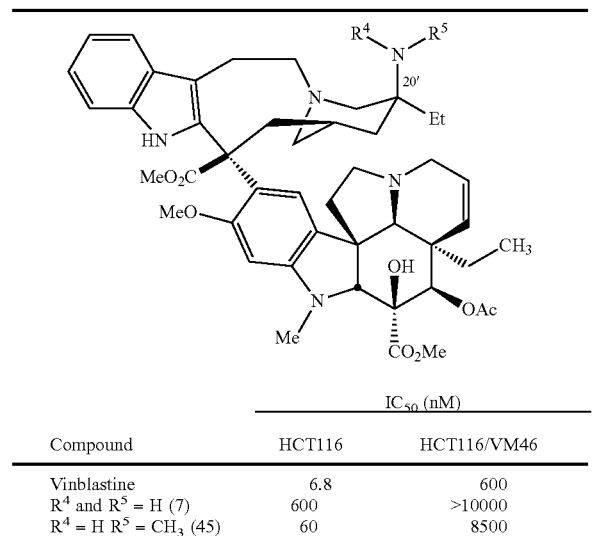

| Compound | HCT116 | HCT116/VM46 |
|---|---|---|
| Vinblastine | 6.8 | 600 |
| R$^4$ and R$^5$ = H (7) | 600 | >10000 |
| R$^4$ = H R$^5$ = CH$_3$ (45) | 60 | 8500 |
| R$^4$ and R$^5$ = CH$_3$ (46) | 980 | >10000 |

The 20'-(methylamino)vinblastine (45) was enlisted to establish whether the active urea derivatives require or

| Compound | X | Y | Z | IC$_{50}$ (nM) HCT116 |
|---|---|---|---|---|
| 1 | | | | 6.8 |
| 39 | NH | O | NMe | 2.8 |
| 43 | NH | S | NMe | 8.7 | benefit from the H-bond donor site of the derivatized C20'-amine. Thus, treatment of 45 with ethyl isocyanate provided the N-methyl urea 47 for comparison with 15. As seen from the data below, there was a 700-fold decrease in activity between 15 and 47 (HCT116), clearly illustrating the importance of a H-bond donor site on the C20'-position. This observation clearly suggests that

| Compound | HCT116 | HCT116/VM46 |
|---|---|---|
| | $IC_{50}$ (nM) | |
| R = H (15) | 0.73 | 90 |
| R = Me (47) | 520 | 8500 | the incorporation of a urea functionality maintains a key H-bond site directly attached to the C20'-position and that it best approximates the acidity of the vinblastine C20'-alcohol, while permitting for further functionalization on the urea terminal nitrogen that maintains or in many cases improves the activity of the compound.

In other recent work, the incorporation of a fluorine atom at the 10'-position provided a potent molecule (48) with an 8-fold improvement in activity over vinblastine itself. [Gotoh et al., ACS Med. Chem. Lett. 2011 2:948-952.] It was of interest to determine whether the incorporation of both the 10'-F substituent and a C20'-urea would have an additive effect in enhancing the potency of vinblastine. An analogue 49 with both functionalities was prepared and evaluated as shown, below. Only a modest improvement in potency was observed in 49 relative

| Compound | HCT116 | HCT116/VM46 |
|---|---|---|
| | $IC_{50}$ (nM) | |
| R = OH, X = H (1) | 6.8 | 600 |
| R = NHCONHEt, X = H (15) | 0.73 | 90 |

| Compound | HCT116 | HCT116/VM46 |
|---|---|---|
| | $IC_{50}$ (nM) | |
| R = OH, X = F (48) | 0.80 | 80 |
| R = NHCONHEt, X = F (49) | 0.62 | 70 | to 15 and 48, suggesting that these modifications are not fully additive. Nonetheless, the modified vinblastine 49 is at least 10-fold more potent than vinblastine exhibiting a sub-nanomolar $IC_{50}$ for cell growth inhibition (620 pM, HCT116) and a nearly 10-fold improved activity against a vinblastine-resistant cell line ($IC_{50}$=70 nM, HCT116/VM46).

Binding to Tubulin.

Given the apparent steric constraints of the tubulin binding site surrounding the vinblastine C20'-center [Gigant et al., Nature 2005 435:519-522] and the size of the C20'-urea substituents that support and improve on the functional potency of vinblastine itself in the cytotoxic cell growth assays, it was not clear whether these effects could be related to their target (tubulin) binding affinity or derived from their impact on other properties of the molecules (e.g., cell permeability, metabolism, solubility). As a result, two representative C20'-urea derivatives 35 and 39 were examined in a well-established tubulin binding assay conducted by measuring the competitive displacement of $^3$H-vinblastine from porcine tubulin [Owellen et al., Biochem. Pharmacol. 1977 26:1213-1219].

Notably, 35 contains the large biphenyl urea substituent yet matches the functional activity of vinblastine, whereas 39 bears the much smaller N,N-dimethylurea whose functional activity slightly exceeds that of vinblastine (3-fold). Importantly, these binding studies confirmed that 39 binds tubulin with a slightly better affinity than vinblastine and further established that even 35, bearing the large biphenyl substituent, remarkably binds with an affinity matching or even slightly exceeding that of vinblastine.

Thus, the effects of the urea 39 as well as 35 observed in the functional assays correlate directly with their target tubulin binding affinities. These unanticipated observations with 35 highlight that the vinblastine interaction with tubulin surrounding the C20'-center is flexible and capable of reorganization to accommodate even a very large substituent. It is notable that this site is adjacent to the nucleotide binding site involving the T5 loop in the N-terminal β1 tubulin nucleotide binding domain and adjacent to the H6 helix and H6-H7 loop that links the nucleotide binding domain to the intermediate domain. It is likely this region is capable of significant reorganization to accommodate the binding of 35 or that the urea substituent may extend into the nucleotide binding site and displace a bound nucleotide.

Tubulin Binding Properties

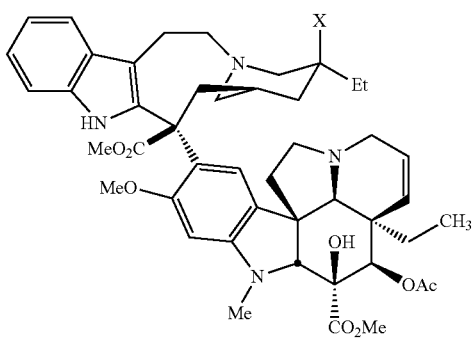

| Compound | % ³H-vinblastine remaining bound[a] | HCT116 IC$_{50}$ (nM) |
|---|---|---|
| 1 | 50.0 | 6.8 |
| 39 | 45.1 ± 3.5 | 2.8 |
| 35 | 48.5 ± 6.9 | 6.9 |

[a]Competitive binding of ligand vs [³H]VBL (1:1) measuring the remaining bound [³H]VBL. Average of 3 repeat determinations, normalized to have dpm (25 μL VLB + 25 μL [³H]VLB) = 50.0%.
1, X = OH (vinblastine)

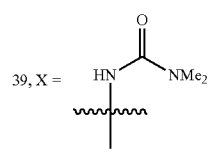

39, X =

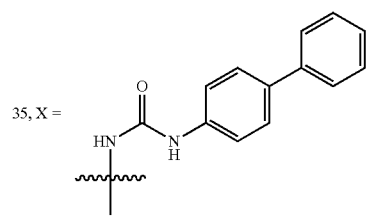 [SMILES: *NC(=O)Nc1ccc(-c2ccccc2)cc1]

35, X =

Further Tubulin Binding Studies

The C20' urea derivative Compound 58 was examined in a tubulin binding assay conducted by measuring the competitive displacement of ³H-vinblastine from porcine tubulin Illustrated below [Owellen et al., *Biochem. Pharmacol.* 1977 26:1213-1219]. The binding studies established that Compound 58 binds tubulin with a higher affinity than vinblastine, establishing that its enhanced potency in the cell growth functional assays correlates directly with its target tubulin binding affinity and suggests that the improved intrinsic activity is a direct result of the inhibition of microtubule formation.

| Compound | % ³H-vinblastine remaining bound[a] | HCT116 IC$_{50}$ (nM) |
|---|---|---|
| 1 | 50.0 | 6.8 |
| 58 | 41.2 | 0.60 |

[a]Competitive binding of ligand versus [³H]VBL (1:1) measuring the remaining bound [³H]VBL. Average of two repeat determinations, normalized to have dpm (25 μL VLB + 25 μL [³H]VLB) = 50.0%.
1, X = OH (vinblastine)

58 X =

To confirm that the exceptional activity observed in our lab would be observed by others, vinblastine (1) and Compounds 55, 57 and 58 were examined offsite at an independent laboratory in a more comprehensive human tumor 15-cell line panel including cell lines of clinical interest from breast, lung, colon, prostate and ovary tissue (below). Compounds 55, 57 and 58 exhibited remarkable potency against all cell lines examined with the exception of MCF-7, with all three compounds displaying at least a 10-fold improvement in activity over vinblastine (range of 10-200-fold more potent).

Cell Growth Inhibition in 15-Cell Line Panel

| Cell Line[a] | IC$_{50}$ (nM) | | | |
|---|---|---|---|---|
| | 1 | 55 | 57 | 58 |
| AU565 | 4.0 | 0.15 | 0.13 | 0.11 |
| NCI-H520 | 4.5 | 0.17 | 0.14 | 0.10 |
| HCC1143 | 3.8 | 0.13 | 0.16 | 0.09 |
| HCC70 | 3.5 | 0.21 | 0.13 | 0.04 |
| HCT116 | 6.8 | 0.22 | 0.26 | 0.16 |
| KPL4 | 2.9 | 0.06 | 0.06 | 0.04 |
| LNCaP-FGC | 5.1 | 0.45 | 0.02 | 0.24 |
| LS174T | 19.6 | 0.46 | 0.30 | 0.45 |
| MCF-7 | >110[b] | >12.5[b] | 2.1 | >12.5[b] |
| MDA-MB-468 | 4.6 | 0.40 | 0.12 | 0.39 |
| SW403 | 7.9 | 0.50 | 1.2 | 0.45 |
| T47D | 5.0 | 0.51 | 0.55 | 0.41 |
| ZR-75-1 | 8.0 | 0.71 | 0.52 | 0.45 |
| PA-1 | 4.6 | 0.11 | 0.19 | 0.11 |
| HCT116/VM46 | >110[b] | 6.4 | 6.6 | 3.5 |

[a]Cell line identities are provided hereinafter.
[b]Highest concentration tested.

Compound 57 exhibited exceptional potency against LNCaP-FGC (20 pM) whereas Compound 58 provided the best activity against the resistant HCT116/VM46 cell line (3.5 nM) in this cell line panel and a reduced differential from the sensitive HCT116 cell line of 20-fold. The average $IC_{50}$ value for vinblastine in this human tumor cell line panel was 6.1 nM, excluding the two cell lines for which it was inactive, and the comparative average $IC_{50}$ values were 310 pM, 200 pM, and 200 pM for Compounds 55, 57 and 58, respectively, representing average enhancements of 30-fold for Compounds 57 and 58 over the activity of vinblastine.

CONCLUSIONS

A remarkable series of previously inaccessible C20'-urea derivatives of vinblastine were prepared and found to match or substantially exceed the potency of vinblastine in functional cell-based growth inhibition assays. In addition to defining structural features of the urea required for or potentiating their activity that are directly related to their relative tubulin binding affinity, the studies established an unprecedented steric tolerance for the size of a C20'-substituent. A H-bond donor on the C20'-position was unequivocally shown to be an important feature of the potent vinblastine analogues. Although this site is known to be critical to the properties of vinblastine and is located deeply embedded in the tubulin bound complex where such substituents would be apparently sterically constrained, the studies revealed that sterically demanding ureas are not only tolerated but that functionalization of this site offers a superb opportunity for enhancing potency as much as 10-fold. In addition to improvements in potency, the C20'-site can also be a superb site for modulating the physical and chemical properties of the drug that impact additional features including Pgp efflux, in vivo drug distribution, selective cellular uptake, and metabolism.

A series of disubstituted C20' urea derivatives of vinblastine were prepared and Compounds 55 and 57-59 were found to not only possess extraordinary potency, but to exhibit further improved activity against the Pgp overexpressing vinblastine-resistant HCT116/VM46 cell line, displaying a reduced differential in activity against the sensitive and resistant HCT116 cell line of only 10- to 20-fold (vs ca. 100-fold for vinblastine).

Compound 57 was found to bind tubulin with a higher affinity than vinblastine, confirming that its enhanced potency observed in the cell growth functional assays correlates with its target tubulin binding affinity. Examination of Compounds 55, 57 and 58 in a human tumor 15-cell line panel revealed that these C20' urea analogs are on average 20- to 30-fold more potent than vinblastine across a broad spectrum of clinically relevant human cancer cell lines (range of 10-200-fold more potent), displaying low pM IC50 values (40-450 pM for 58). Clearly, the C20' position within vinblastine represents a key site amenable to functionalization capable of simultaneously improving tubulin binding affinity, substantially enhancing biological potency, and presumably decreasing relative Pgp transport central to clinical resistance.

EXPERIMENTAL SECTION

General Procedures

All commercial reagents were used without further purification unless otherwise noted. THF was distilled prior to use. All reactions were performed in oven-dried (200° C.) glassware and under an inert atmosphere of anhydrous Ar unless otherwise noted.

Column chromatography was performed with silica gel 60. TLC was performed on Whatman® silica gel (250 µm) $F_{254}$ glass plates and spots visualized by UV. PTLC was performed on Whatman® silica gel (250 and 500 µm) $F_{254}$ glass plates.

Optical rotations were determined on a Rudolph Research Analytical Autopol® III automatic polarimeter using the sodium D line ($\lambda$=589 nm) at room temperature (23° C.) and are reported as follows: $[\alpha]^D_{23}$, concentration (c=g/100 mL), and solvent. FT-IR spectroscopy was recorded on a Nicolet 380 FT-IR instrument.

$^1$H NMR was recorded on a Bruker 600 MHz spectrometer. Chemical shifts are reported in ppm from an internal standard of residual $CHCl_3$ ($\delta$ 7.26 for $^1$H). Proton chemical data are reported as follows: chemical shift ($\delta$), multiplicity (ovlp=overlapping, br=broad, s=singlet, d=doublet, t=triplet, q=quartet, m=multiplet), coupling constant, and integration.

High resolution mass spectra were obtained on an Agilent ESI-TOF/MS using Agilent ESI-L low concentration tuning mix as internal high resolution calibration standards. The purity of each tested compound (>95%) was determined on an Agilent 1100 LC/MS instrument using a ZORBAX® SB-C18 column (3.5 mm, 4.6 mm×50 mm, with a flow rate of 0.75 mL/minute and detection at 220 and 254 nm) with a 10-98% acetonitrile/water/0.1% formic acid gradient (two different gradients).

Cell Line Key

AU565 (Breast, overexpression of her2/neu), NCI-H520 (Lung), HCC1143 (Breast, triple negative), HCC70 (Breast, overexpression of p53), HCT116 (Colon), KPL4 (Breast, overexpression of erbB2), LNCaP-FGC (Prostate), LS174T (Colon, high levels of MUC2 mRNA), MCF-7 (Breast, overexpression of her2/neu), MDA-MB-468 (Breast, triple negative, amplified EGFR), SW403 (Colon, $KRAS^{G12V}$ mutation), T47D (Breast, mutant p53), ZR-75-1 (Breast, overexpression of her2), PA-1 (Ovary, overexpression of AIB1), HCT116/VM46 (Colon, vinblastine resistant).

General Methods for the Synthesis of Ureas.

Method 1:

A solution of 20'-aminovinblastine (7, 3.5 mg, 0.004 mmol) in THF (3 mL) was treated with an isocyanate (0.008 mmol). The reaction mixture was stirred for 2 hours at 25° C. and then was quenched with the addition of distilled $H_2O$ (3 mL). The mixture was extracted with 10% MeOH in $CH_2Cl_2$ and the combined organic extracts were washed with saturated aqueous NaCl (3 mL). The organic layer was dried over $Na_2SO_4$, and concentrated under reduced pressure. Preparative thin layer chromatography (PTLC; $SiO_2$, EtOAc:MeOH:$Et_3$N=97:3:3) provided the urea (15, 19-21, 23-32, and 34-35); yields (35-98%). Isocyanates used include: ethyl isocyanate, n-butyl isocyanate, t-butyl isocyanate, cyclohexyl isocyanate, phenyl isocyanate, benzyl isocyanate, phenethyl isocyanate, o-methoxyphenyl isocyanate, m-methoxyphenyl isocyanate, p-methoxyphenyl isocyanate, p-fluoro-phenyl isocyanate, p-chlorophenyl isocyanate, p-tolyl isocyanate, p-trifluoromethylphenyl isocyanate, furfuryl isocyanate and p-biphenyl isocyanate.

Method 2:

A solution of 20'-aminovinblastine (7, 5.7 mg, 0.007 mmol) in THF (3 mL) was treated with 4-nitrophenyl chloroformate (2.1 mg, 0.011 mmol, 1.5 equiv). The reaction mixture was stirred for 4 hours at 25° C. and then was concentrated under reduced pressure. PTLC ($SiO_2$, EtOAc:MeOH=95:5) provided 13 (4.6 mg, 67%, off white solid). A solution of 13 (4.0 mg, 0.004 mmol) in THF (3 mL) was treated with an amine (0.008 mmol). The reaction mixture was stirred for 1 hour at 25° C. and then was quenched with the addition of distilled $H_2O$ (3 mL). The mixture was extracted with 10% MeOH in $CH_2Cl_2$, and the combined organic extracts were washed with saturated aqueous NaCl (3 mL). The organic layer was dried over $Na_2SO_4$, and concentrated under reduced pressure. PTLC ($SiO_2$, EtOAc:MeOH:$Et_3$N=97:3:3) provided the urea (14, 16-18, 22, 33, 39-42 and 52-59); yields (40-99%). The amines used include: methylamine, propylamine, isopropylamine, cyclopropylamine, dimethylamine, diethylamine, 2-(aminomethyl)pyridine, morpholine, piperidine, ethanolamine, pyrrolidine, N-methylpiperazine, tetrahydropyridine, 4-phenylpiperidine, 1,2,3,4-tetrahydroisoquinoline, isoindoline and 4-methoxyisoindoline.

General Methods for the Synthesis of Thioureas.

Method 3:

A solution of 20'-aminovinblastine (7, 8.0 mg, 0.010 mmol) in THF (4 mL) was treated with an isothiocyanate (0.031 mmol). The reaction mixture was stirred for 2 hours at 25° C. and then was quenched with the addition of distilled $H_2O$ (3 mL). The mixture was extracted with 10% MeOH in $CH_2Cl_2$, and the combined organic extracts were washed with saturated aqueous NaCl (3 mL). The organic layer was dried over $Na_2SO_4$, and concentrated under reduced pressure. PTLC ($SiO_2$, EtOAc:MeOH:Et$_3$N=97:3:3) provided the thiourea (37); yields (70%). The isothiocyanate used: phenylisothiocyanate.

Method 4:

A solution of 20'-aminovinblastine (7, 8.2 mg, 0.010 mmol) in THF (3 mL) was treated with carbon disulfide (915 μL, 15 mmol). The reaction mixture was stirred for 13 hours and then was quenched with the addition of distilled $H_2O$ (5 mL). The mixture was extracted with 10% MeOH in $CH_2Cl_2$, and washed with saturated aqueous NaCl (2 mL). The organic layer was dried over $Na_2SO_4$, and concentrated under reduced pressure. PTLC ($SiO_2$, EtOAc:MeOH:Et$_3$N=97:3:3) provided 5 (7.0 mg, 82%, white solid). [Leggans et al., *Org. Lett.* 2012 14:1428-1431.]

A solution of 20'-isothiocyanovinblastine (5, 6.0 mg, 0.007 mmol) in THF (3 mL) was treated with an amine (0.011 mmol). The reaction mixture was stirred for 1 hour at 25° C. and then was quenched with the addition of distilled $H_2O$ (3 mL). The mixture was extracted with 10% MeOH in $CH_2Cl_2$, and the combined extracts were washed with saturated aqueous NaCl (3 mL). The organic layer was dried over $Na_2SO_4$, and concentrated under reduced pressure. PTLC ($SiO_2$, EtOAc:MeOH:Et$_3$N=97:3:3) provided the thiourea (36, 38, and 43); yields (26-92%). The amines used include: cyclohexylamine, 4-fluorophenethylamine and dimethylamine.

General Method for the Synthesis of Ureas with N,N-Disubstituted Distal Amino Groups A solution of 20'-aminovinblastine[1] (5.7 mg, 0.007 mmol) in THF (3 mL) was treated with 4-nitrophenyl chloroformate (2.1 mg, 0.011 mmol, 1.5 equiv) and triethylamine (10 μL, 0.07 mmol, 10 equiv). The reaction mixture was stirred at 25° C. until consumption of 20'-aminovinblastine was observed by LCMS (typically 4 hours) and then the secondary amine was added (0.07 mmol). The reaction mixture was stirred at 25° C. until the reaction was complete by LCMS (typically 3-4 h) and then concentrated under a stream of $N_2$. PTLC ($SiO_2$, EtOAc:MeOH=94:6) provided the urea (Compounds 52-59); yields (34-79%).

Physical Data for Specific Compounds

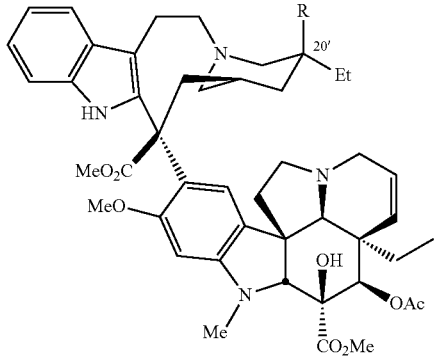

Compound (R=20'-NHCO$_2$C$_6$H$_4$NO$_2$) 13

Yield: 67%, Method 2. $^1$H NMR (600 MHz, CDCl$_3$) δ 9.87 (br s, 1H), 8.11 (d, J=9.2 Hz, 2H), 8.04 (br s, 1H), 7.53 (d, J=7.8 Hz, 1H), 7.18-7.14 (m, 1H), 7.14-7.08 (m, 2H), 6.76 (d, J=9.1 Hz, 2H), 6.63 (s, 1H), 6.11 (s, 1H), 5.85 (dd, J=10.0, 3.9 Hz, 1H), 5.48 (s, 1H), 5.30 (d, J=9.8 Hz, 1H), 4.00 (t, J=13.2 Hz 1H), 3.81 (s, 3H), 3.79 (s, 3H), 3.72 (s, 1H), 3.63 (s, 3H), 3.60-3.55 (m, 4H), 3.43 (d, J=13.6 Hz, 1H), 3.37 (dd, J=15.9, 4.5 Hz, 1H), 3.35-3.26 (m, 2H), 3.20-3.13 (m, 2H), 2.98 (d, J=13.8 Hz, 1H), 2.85-2.77 (m, 2H), 2.70 (s, 3H), 2.46-2.42 (m, 1H), 2.35 (d, J=11.9 Hz, 1H), 2.24 (d, J=13.0 Hz, 1H), 2.20-2.13 (m, 1H), 2.11 (s, 3H), 1.85-1.76 (m, 2H), 1.64 (d, J=14.8 Hz, 1H), 1.47-1.40 (m, 2H), 1.37-1.29 (m, 2H), 0.96 (t, J=7.4 Hz, 3H), 0.83 (t, J=7.4 Hz, 3H); IR (film) $v_{max}$ 3467, 2924, 1736, 1218 cm$^{-1}$; HRESI-TOF m/z 975.4492 (C$_{53}$H$_{62}$N$_6$O$_{12}$+H$^+$, required 975.4498); [α]$_D^{23}$ −13 (c 0.1, CHCl$_3$).

Compound (R=20'-NHCONHCH$_3$) 14

Yield: 85%, Method 2. $^1$H NMR (600 MHz, CDCl$_3$) δ 9.83 (br s, 1H), 7.97 (br s, 1H), 7.51 (d, J=7.8 Hz, 1H), 7.19-7.13 (m, 1H), 7.13-7.07 (m, 2H), 6.64 (s, 1H), 6.09 (s, 1H), 5.86 (dd, J=10.0, 4.4 Hz, 1H), 5.47 (s, 1H), 5.31 (d, J=10.7 Hz, 2H), 4.54 (br s, 1H), 4.33 (br s, 1H), 3.84 (t, J=13.2 Hz 1H), 3.80 (s, 6H), 3.74 (s, 1H), 3.60 (s, 3H), 3.39-3.36 (m, 2H), 3.32-3.21 (m, 3H), 3.20-3.10 (m, 2H), 2.86 (d, J=4.8 Hz, 3H), 2.83 (d, J=16.6 Hz, 1H), 2.71 (s, 3H), 2.68 (s, 1H), 2.58 (d, J=13.8 Hz, 1H), 2.45 (dd, J=16.9, 10.5 Hz, 1H), 2.38 (d, J=12.8 Hz, 1H), 2.20-2.15 (m, 2H), 2.11 (s, 3H), 1.85-1.74 (m, 4H), 1.69 (d, J=13.7 Hz, 2H), 1.44-1.30 (m, 2H), 0.82 (t, J=7.4 Hz, 3H), 0.77 (t, J=7.4 Hz, 3H); IR (film) $v_{max}$ 3539, 2870, 1721, 1554, 1461, 1223, 1039, 712 cm$^{-1}$; HRESI-TOF m/z 867.4631 (C$_{53}$H$_{62}$N$_6$O$_{12}$+H$^+$, required 867.4651); [α]$_D^{23}$ −1.5 (c 0.05, CHCl$_3$).

Compound (R=20'-NHCONHCH$_2$CH$_3$) 15

Yield: 95%, Method 1. $^1$H NMR (600 MHz, CDCl$_3$) δ 9.84 (br s, 1H), 7.98 (br s, 1H), 7.51 (d, J=7.8 Hz, 1H), 7.19-7.14 (m, 1H), 7.14-7.07 (m, 2H), 6.64 (s, 1H), 6.09 (s, 1H), 5.86 (dd, J=9.9, 4.0 Hz, 1H), 5.47 (s, 1H), 5.31 (d, J=9.8 Hz, 1H), 4.59 (br s, 1H), 4.29 (br s, 1H), 3.83 (t, J=12.0 Hz, 1H), 3.80 (s, 6H), 3.74 (s, 1H), 3.60 (s, 3H), 3.37 (d, J=15.0 Hz, 2H), 3.34-3.19 (m, 4H), 3.18-3.13 (m, 2H), 2.83 (d, J=16.0 Hz, 1H), 2.71 (s, 3H), 2.68 (s, 1H), 2.57 (d, J=13.1 Hz, 1H), 2.47-2.43 (m, 1H), 2.38 (d, J=13.4 Hz, 1H), 2.20-2.15 (m, 2H), 2.11 (s, 3H), 1.86-1.73 (m, 4H), 1.68 (d, J=14.3 Hz, 2H), 1.41-1.38 (m, 4H), 1.19 (t, J=7.2 Hz, 3H), 0.82 (t, J=7.4 Hz, 3H), 0.77 (t, J=7.4 Hz, 3H); IR (film) $v_{max}$ 3463, 2921, 1739, 1500, 1459, 1228, 1039, 739 cm$^{-1}$; HRESI-TOF m/z 881.4797 (C$_{49}$H$_{64}$N$_6$O$_9$+H$^+$, required 881.4808); [α]$_D^{23}$ +5.4 (c 0.08, CHCl$_3$).

Compound (R=20'-NHCONHCH$_2$CH$_2$CH$_3$) 16

Yield: 40%, Method 2. $^1$H NMR (600 MHz, CDCl$_3$) δ 9.84 (br s, 1H), 7.98 (br s, 1H), 7.51 (d, J=7.8 Hz, 1H), 7.18-7.14 (m, 1H), 7.14-7.08 (m, 2H), 6.64 (s, 1H), 6.09 (s, 1H), 5.86 (dd, J=10.1, 4.3 Hz, 1H), 5.47 (s, 1H), 5.31 (d, J=9.8 Hz, 1H), 4.63 (br s, 1H), 4.28 (br s, 1H), 3.83 (t, J=12.0 Hz, 1H), 3.80 (s, 6H), 3.74 (s, 1H), 3.60 (s, 3H), 3.37 (dd, J=15.9, 4.7 Hz, 2H), 3.34-3.27 (m, 2H), 3.27-3.11 (m, 4H), 2.83 (d, J=16.2 Hz, 1H), 2.71 (s, 3H), 2.68 (s, 1H), 2.57 (d, J=13.8 Hz, 1H), 2.47-2.42 (m, 1H), 2.38 (d, J=13.1 Hz, 1H), 2.24-2.15 (m, 2H), 2.09 (s, 3H), 1.87-1.75 (m, 4H), 1.60-1.52 (m, 6H), 1.40-1.34 (m, 2H), 0.95 (t, J=7.4 Hz, 3H), 0.82 (t, J=7.4 Hz, 3H), 0.77 (t, J=7.4 Hz, 3H); IR (film) $v_{max}$ 3436, 2952, 1739, 1547, 1459, 1243, 1032, 755 cm$^{-1}$; HRESI-TOF m/z 895.4953 (C$_{50}$H$_{66}$N$_6$O$_9$+H$^+$, required 895.4964); [α]$_D^{23}$ +4.0 (c 0.05, CHCl$_3$).

Compound (R=20'-NHCONHCH(CH$_3$)$_2$) 17

Yield: 59%, Method 2. $^1$H NMR (600 MHz, CDCl$_3$) δ 9.84 (br s, 1H), 8.00 (br s, 1H), 7.52 (d, J=7.9 Hz, 1H), 7.17-7.08 (m, 3H), 6.65 (s, 1H), 6.09 (s, 1H), 5.87 (dd, J=10.1, 3.7 Hz, 1H), 5.47 (s, 1H), 5.31 (d, J=9.3 Hz, 1H), 4.29 (br s, 1H), 4.14 (br s, 1H), 3.96-3.91 (m, 1H), 3.81-3.77 (m, 1H), 3.80 (s, 3H), 3.79 (s, 3H), 3.74 (s, 1H), 3.73-3.71 (m, 1H), 3.60 (s, 3H), 3.37 (d, J=14.8 Hz, 2H), 3.34-3.26 (m, 2H), 3.23 (t', J=11.9 Hz, 1H), 3.18-3.11 (m, 2H), 2.83 (d, J=16.0 Hz, 1H), 2.71 (s, 3H), 2.67 (s, 1H), 2.56 (d, J=13.6 Hz, 1H), 2.47-2.43 (m, 1H), 2.36 (d, J=14.4 Hz, 1H), 2.20-2.15 (m, 2H), 2.11 (s, 3H), 1.86-1.73 (m, 4H), 1.47-1.42 (m, 1H), 1.37-1.29 (m, 3H), 1.20 (dd, J=6.4, 2.5 Hz, 6H), 0.82 (t, J=7.4 Hz, 3H), 0.77 (t, J=7.4 Hz, 3H); IR (film) $v_{max}$ 3471, 3323, 2923, 1741, 1459, 1239, 1041 cm$^{-1}$; HRESI-TOF m/z 917.4761 ($C_{50}H_{66}N_6O_9$+Na$^+$, required 917.4783); $[\alpha]_D^{23}$+6.1 (c 0.1, CHCl$_3$).

Compound (R=20'-NHCONHCH(CH$_2$)$_2$) 18
Yield: 70%, Method 2. $^1$H NMR (600 MHz, CDCl$_3$) δ 9.86 (br s, 1H), 8.02 (br s, 1H), 7.50 (d, J=7.8 Hz, 1H), 7.18-7.13 (m, 1H), 7.13-7.07 (m, 2H), 6.62 (s, 1H), 6.10 (s, 1H), 5.85 (dd, J=10.2, 4.4 Hz, 1H), 5.47 (s, 1H), 5.30 (d, J=6.6 Hz, 1H), 5.17 (s, 1H), 4.66 (s, 1H), 3.91 (t, J=13.8 Hz, 1H), 3.80 (s, 6H), 3.74 (s, 1H), 3.56 (s, 3H), 3.41-3.13 (m, 6H), 3.08-3.00 (m, 2H), 2.83 (d, J=16.2 Hz, 1H), 2.77 (br s, 1H), 2.71 (s, 3H), 2.70-2.68 (m, 1H), 2.67 (s, 1H), 2.63 (d, J=13.5 Hz, 1H), 2.47-2.43 (m, 1H), 2.38 (d, J=12.1 Hz, 1H), 2.24 (d, J=14.2 Hz, 1H), 2.19 (dd, J=12.9, 7.7 Hz, 1H), 2.15 (s, 3H), 2.11 (s, 3H), 1.86-1.70 (m, 4H), 1.52-1.49 (m, 2H), 0.81 (t, J=7.3 Hz, 3H), 0.76 (t, J=7.3 Hz, 3H), 0.70-0.69 (m, 2H), 0.50-0.48 (m, 2H); IR (film) $v_{max}$ 3629, 2952, 1740, 1506, 1458, 1245, 998, 748 cm$^{-1}$; HRESI-TOF m/z 893.4792 ($C_{50}H_{64}N_6O_9$+H$^+$, required 893.4808); $[\alpha]_D^{23}$+19 (c 0.09, CHCl$_3$).

Compound (R=20'-NHCONHCH$_2$CH$_2$CH$_2$CH$_3$) 19
Yield: 45%, Method 1. $^1$H NMR (600 MHz, CDCl$_3$) δ 9.85 (br s, 1H), 7.98 (br s, 1H), 7.50 (d, J=7.8 Hz, 1H), 7.18-7.13 (m, 1H), 7.13-7.07 (m, 2H), 6.64 (s, 1H), 6.09 (s, 1H), 5.86 (dd, J=10.2, 4.4 Hz, 1H), 5.46 (s, 1H), 5.31 (d, J=11.1 Hz, 1H), 4.56 (br s, 1H), 4.27 (br s, 1H), 3.80 (s, J=1.6 Hz, 6H), 3.74 (s, 1H), 3.60 (s, 3H), 3.37 (dd, J=15.9, 4.7 Hz, 2H), 3.31-3.20 (m, 4H), 3.15 (br s, 2H), 3.09 (dd, J=14.5, 7.2 Hz, 4H), 2.83 (d, J=16.2 Hz, 1H), 2.71 (s, 3H), 2.68 (s, 1H), 2.55 (d, J=13.8 Hz, 1H), 2.47-2.43 (m, 1H), 2.38 (d, J=12.1 Hz, 1H), 2.20-2.15 (m, 2H), 2.11 (s, 3H), 2.07 (s, 1H), 1.86-1.72 (m, 4H), 1.56-1.49 (m, 2H), 1.38-1.33 (m, 4H), 0.93 (t, J=7.3 Hz, 3H), 0.82 (t, J=7.3 Hz, 3H), 0.77 (t, J=7.3 Hz, 3H); IR (film) $v_{max}$ 3544, 2952, 1736, 1501, 1458, 1240, 1030, 761 cm$^{-1}$; HRESI-TOF m/z 909.5106 ($C_{51}H_{68}N_6O_9$+H$^+$, required 909.5121); $[\alpha]_D^{23}$+14 (c 0.06, CHCl$_3$).

Compound (R=20'-NHCONHC(CH$_3$)$_3$) 20
Yield: 45%, Method 1. $^1$H NMR (600 MHz, CDCl$_3$) δ 9.83 (br s, 1H), 7.99 (br s, 1H), 7.53 (d, J=8.0 Hz, 1H), 7.19-7.14 (m, 1H), 7.13-7.07 (m, 2H), 6.65 (s, 1H), 6.09 (s, 1H), 5.86 (dd, J=10.1, 3.9 Hz, 1H), 5.47 (s, 1H), 5.31 (d, J=10.2 Hz, 1H), 4.54 (br s, 1H), 4.10 (br s, 1H), 3.83 (t, J=14.1 Hz, 1H), 3.80 (s, 3H), 3.78 (s, 3H), 3.74 (s, 1H), 3.60 (s, 3H), 3.40-3.22 (m, 5H), 3.17-3.12 (m, 2H), 2.71 (s, 3H), 2.68 (s, 1H), 2.54 (d, J=13.6 Hz, 1H), 2.47-2.42 (m, 1H), 2.35 (d, J=13.4 Hz, 1H), 2.21-2.14 (m, 2H), 2.11 (s, 3H), 1.87-1.75 (m, 2H), 1.73-1.62 (m, 1H), 1.49-1.41 (m, 2H), 1.38 (s, 9H), 1.37-1.31 (m, 2H), 0.82 (t, J=7.4 Hz, 3H), 0.77 (t, J=7.4 Hz, 3H); IR (film) $v_{max}$ 3457, 2941, 1741, 1556, 1458, 1244, 1036, 741 cm$^{-1}$; HRESI-TOF m/z 909.5128 ($C_{51}H_{68}N_6O_9$+H$^+$, required 909.5121); $[\alpha]_D^{23}$+3.0 (c 0.1, CHCl$_3$).

Compound (R=20'-NHCONHC$_6$H$_{11}$) 21
Yield: 51%, Method 1. $^1$H NMR (600 MHz, CDCl$_3$) δ 9.84 (br s, 1H), 7.99 (br s, 1H), 7.52 (d, J=7.9 Hz, 1H), 7.20-7.14 (m, 1H), 7.14-7.07 (m, 2H), 6.64 (s, 1H), 6.09 (s, 1H), 5.86 (dd, J=10.3, 4.1 Hz, 1H), 5.47 (s, 1H), 5.31 (d, J=9.3 Hz, 1H), 4.53 (br s, 1H), 4.22 (br s, 1H), 4.02 (d, J=9.0 Hz, 1H), 3.83 (t, J=12.9 Hz, 1H), 3.79 (s, 3H), 3.79 (s, 3H), 3.74 (s, 1H), 3.60 (s, 3H), 3.50-3.45 (m, 1H), 3.39-3.21 (m, 3H), 3.16-3.12 (m, 2H), 2.83 (d, J=16.1 Hz, 1H), 2.71 (s, 3H), 2.67 (s, 1H), 2.55 (d, J=13.5 Hz, 1H), 2.47-2.42 (m, 1H), 2.37 (d, J=12.7 Hz, 1H), 2.21-2.14 (m, 2H), 2.11 (s, 3H), 2.04-1.90 (m, 2H), 1.86-1.74 (m, 4H), 1.64-1.59 (m, 2H), 1.37-1.31 (m, 6H), 1.20-1.02 (m, 6H), 0.82 (t, J=7.4 Hz, 3H), 0.77 (t, J=7.4 Hz, 3H); IR (film) $v_{max}$ 3460, 2919, 1738, 1556, 1459, 1242, 1033, 752 cm$^{-1}$; HRESI-TOF m/z 935.5276 ($C_{53}H_{70}N_6O_9$+H$^+$, required 935.5277); $[\alpha]_D^{23}$+3.8 (c 0.09, CHCl$_3$).

Compound (R=20'-NHCONHCH$_2$CH$_2$OH) 22
Yield: 60%, Method 2. $^1$H NMR (600 MHz, CDCl$_3$) δ 9.78 (br s, 1H), 7.99 (br s, 1H), 7.52 (d, J=7.8 Hz, 1H), 7.19-7.09 (m, 3H), 6.69 (s, 1H), 6.08 (s, 1H), 5.89-5.85 (m, 1H), 5.48 (s, 1H), 5.31 (d, J=11.8 Hz, 1H), 4.59 (br s, 1H), 3.83-3.72 (m, 4H), 3.80 (s, 3H), 3.79 (s, 3H), 3.76 (s, 1H), 3.57 (s, 3H), 3.57-3.54 (m, 1H), 3.42-3.37 (m, 3H), 3.34-3.29 (m, 1H), 3.26-3.17 (m, 4H), 3.08-3.03 (m, 1H), 2.87 (br s, 1H), 2.82 (d, J=16.0 Hz, 1H), 2.72 (s, 3H), 2.68 (s, 1H), 2.60-2.42 (m, 1H), 2.33-2.17 (m, 1H), 2.14-2.09 (m, 1H), 2.11 (s, 3H), 1.97-1.77 (m, 2H), 1.75-1.64 (m, 3H), 1.50-1.45 (m, 1H), 1.38-1.34 (m, 2H), 1.16 (dd, J=14.3, 4.6 Hz, 2H), 0.83-0.81 (m, 3H), 0.77 (t, J=7.1 Hz, 3H); IR (film) $v_{max}$ 3399, 2927, 1738, 1502, 1458, 1232, 1040 cm$^{-1}$; HRESI-TOF m/z 897.4753 ($C_{49}H_{64}N_6O_{10}$+H$^+$, required 897.4756); $[\alpha]_D^{23}$−14 (c 0.2, CHCl$_3$).

Compound (R=20'-NHCONHC$_6$H$_5$) 23
Yield: 87%, Method 1. $^1$H NMR (600 MHz, CDCl$_3$) δ $^1$H NMR (600 MHz, CDCl$_3$) δ 9.87 (br s, 1H), 7.98 (br s, 1H), 7.47 (d, J=8.1 Hz, 1H), 7.45 (d, J=8.0 Hz, 2H), 7.31 (t, J=7.8 Hz, 2H), 7.16-7.14 (m, 1H), 7.13-7.05 (m, 3H), 6.62 (s, 1H), 6.09 (s, 1H), 5.85 (dd, J=10.3, 4.6 Hz, 1H), 5.47 (s, 1H), 5.31 (d, J=9.4 Hz, 1H), 4.80 (s, 1H), 3.80 (s, 6H), 3.74 (s, 1H), 3.60 (s, 3H), 3.39-3.35 (m, 2H), 3.32-3.28 (m, 1H), 3.22-3.18 (m, 1H), 3.10 (s, 3H), 2.82 (d, J=16.3 Hz, 1H), 2.71 (s, 3H), 2.67 (s, 1H), 2.59 (d, J=13.8 Hz, 1H), 2.47-2.42 (m, 1H), 2.36-2.28 (m, 2H), 2.25-2.13 (m, 2H), 2.11 (s, 3H), 2.04 (s, 1H), 1.85-1.76 (m, 3H), 1.71-1.65 (m, 2H), 1.64-1.54 (m, 2H), 1.24-1.20 (m, 2H), 0.82 (t, J=7.4 Hz, 3H), 0.80 (t, J=7.4 Hz, 3H); IR (film) $v_{max}$ 3468, 2940, 1742, 1501, 1460, 1237, 1031, 760 cm$^1$; HRESI-TOF m/z 929.4807 ($C_{53}H_{64}N_6O_9$+H$^+$, required 929.4807); $[\alpha]_D^{23}$+16 (c 0.9, CHCl$_3$).

Compound (R=20'-NHCONH(4-fluorophenyl)) 24
Yield: 47%, Method 1. $^1$H NMR (600 MHz, CDCl$_3$) δ 9.81 (br s, 1H), 7.97 (br s, 1H), 7.49 (d, J=8.1 Hz, 1H), 7.42 (dd, J=8.8, 4.8 Hz, 2H), 7.18-7.14 (m, 1H), 7.12-7.08 (m, 2H), 7.01 (t, J=8.6 Hz, 2H), 6.63 (s, 1H), 6.09 (s, 1H), 5.86 (dd, J=10.2, 4.5 Hz, 1H), 5.47 (s, 1H), 5.31 (d, J=12.1 Hz, 1H), 4.71 (br s, 1H), 3.80 (s, 6H), 3.75 (s, 1H), 3.61 (s, 3H), 3.40-3.36 (m, 2H), 3.32-3.28 (m, 1H), 3.21-3.06 (m, 4H), 2.82 (d, J=16.5 Hz, 1H), 2.71 (s, 3H), 2.67 (s, 1H), 2.59 (d, J=13.7 Hz, 1H), 2.47-2.42 (m, 1H), 2.34 (d, J=12.7 Hz, 1H), 2.20-2.15 (m, 2H), 2.11 (s, 3H), 1.85-1.75 (m, 4H), 1.59-1.50 (m, 4H), 1.23-1.21 (m, 2H), 0.82 (t, J=7.4 Hz, 3H), 0.79 (t, J=7.4 Hz, 3H); IR (film) $v_{max}$ 3490, 2921, 1745, 1509, 1455, 1228, 1043, 736 cm$^{-1}$; HRESI-TOF m/z 947.4726 ($C_{53}H_{63}FN_6O_9$+H$^+$, required 947.4713); $[\alpha]_D^{23}$−4.4 (c 0.08, CHCl$_3$).

Compound (R=20'-NHCONH(4-chlorophenyl)) 25
Yield: 63%, Method 1. $^1$H NMR (600 MHz, CDCl$_3$) δ 9.80 (br s, 1H), 7.95 (br s, 1H), 7.40 (d, J=7.9 Hz, 2H), 7.38 (d, J=8.1 Hz, 2H), 7.19-7.07 (m, 5H), 6.65 (s, 1H), 6.08 (s, 1H), 5.86 (dd, J=10.2, 4.5 Hz, 1H), 5.47 (s, 1H), 5.31 (d, J=12.1 Hz, 1H), 4.81 (br s, 1H), 3.79 (s, 6H), 3.75 (s, 1H), 3.60 (s, 3H), 3.36 (d, J=15.7 Hz, 2H), 3.31-3.26 (m, 2H), 3.22-3.15 (m, 2H), 3.01-2.91 (m, 1H), 2.82 (d, J=15.7 Hz, 1H), 2.72 (s, 3H), 2.67 (s, 1H), 2.61-2.55 (m, 2H), 2.49-2.43 (m, 2H), 2.21-2.14 (m, 2H), 2.10 (s, 3H), 1.83-1.74 (s, 4H), 1.36-1.27 (m, 4H), 1.16-1.04 (m, 2H), 0.82 (t, J=7.4 Hz, 3H), 0.79 (t, J=7.4 Hz, 3H); IR (film) $v_{max}$ 3376, 2923, 1736, 1493, 1455, 1240, 1090, 765 cm$^{-1}$; HRESI-TOF m/z 963.4407 ($C_{53}H_{63}ClN_6O_9$+H$^+$, required 963.4418); $[\alpha]_D^{23}$+21 (c 0.07, CHCl$_3$).

Compound (R=20'-NHCONH(4-methylphenyl)) 26
Yield: 40%, Method 1. $^1$H NMR (600 MHz, CDCl$_3$) δ 9.86 (br s, 1H), 7.99 (br s, 1H), 7.47 (d, J=7.9 Hz, 1H), 7.33 (d, J=8.1 Hz, 2H), 7.18-7.07 (m, 3H), 6.61 (s, 1H), 6.08 (s, 1H), 5.85 (d, J=5.9 Hz, 1H), 5.47 (s, 1H), 5.30 (d, J=10.3 Hz, 1H), 4.74 (br s, 1H), 4.30 (br s, 1H), 3.80 (s, 3H), 3.79 (s, 3H), 3.74 (s, 1H), 3.67-3.62 (m, 3H), 3.61 (s, 3H), 3.40-3.34 (m, 2H), 3.31-3.27 (m, 1H), 3.20-3.16 (m, 1H), 2.81 (d, J=15.7 Hz, 1H), 2.71 (s, 3H), 2.66 (s, 1H), 2.58 (d, J=13.3 Hz, 1H), 2.46-2.41 (m, 1H), 2.32 (s, 3H), 2.24-2.14 (m, 2H), 2.11 (s, 3H), 2.03 (s, 1H), 1.87 (d, J=13.8 Hz, 2H), 1.84-1.76 (m, 2H), 1.63-1.53 (m, 4H), 1.38-1.34 (m, 2H), 1.21 (dd, J=14.5, 5.7 Hz, 2H), 0.81 (t, J=7.6 Hz, 3H), 0.78 (t, J=7.6 Hz, 3H); IR (film) $\nu_{max}$ 3369, 2912, 1722, 1507, 1445, 1230, 1017, 729 cm$^{-1}$; HRESI-TOF m/z 943.4949 ($C_{54}H_{66}N_6O_9$+H$^+$, required 943.4964); $[\alpha]_D^{23}$+36 (c 0.1, CHCl$_3$).

Compound (R=20'-NHCONH(4-trifluoro-methylphenyl)) 27

Yield: 60%, Method 1. $^1$H NMR (600 MHz, CDCl$_3$) δ 9.82 (br s, 1H), 7.94 (br s, 1H), 7.58 (d, J=8.6 Hz, 2H), 7.51 (d, J=8.6 Hz, 2H), 7.48 (d, J=7.9 Hz, 1H), 7.18-7.14 (m, 1H), 7.13-7.07 (m, 2H), 6.65 (s, 1H), 6.09 (s, 1H), 5.87 (dd, J=10.0, 4.2 Hz, 1H), 5.46 (s, 1H), 5.31 (d, J=10.3 Hz, 1H), 4.99 (s, 1H), 3.90-3.84 (m, 2H), 3.80 (s, 6H), 3.75 (s, 1H), 3.67-3.63 (m, 3H), 3.61 (s, 3H), 3.40-3.36 (m, 2H), 3.33-3.29 (m, 1H), 3.27-3.20 (m, 1H), 3.13-3.10 (m, 1H), 2.83 (d, J=15.8 Hz, 1H), 2.72 (s, 3H), 2.68 (d, J=11.9 Hz, 1H), 2.60 (d, J=13.8 Hz, 1H), 2.48-2.43 (m, 1H), 2.40 (d, J=13.3 Hz, 1H), 2.33-2.24 (m, 2H), 2.20-2.15 (m, 1H), 2.10 (s, 3H), 2.01 (s, 1H), 1.90-1.87 (m, 2H), 1.84-1.75 (m, 2H), 1.66 (d, J=14.9 Hz, 2H), 1.40-1.32 (m, 2H), 0.82 (t, J=7.2 Hz, 6H); IR (film) $\nu_{max}$ 3334, 2931, 1716, 1537, 1472, 1232, 1023, 745 cm$^{-1}$; HRESI-TOF m/z 997.4685 ($C_{54}H_{63}F_3N_6O_9$+H$^+$, required 997.4681); $[\alpha]_D^{23}$−18 (c 0.04, CHCl$_3$).

Compound (R=20'-NHCONH(4-methoxyphenyl)) 28

Yield: 36%, Method 1. $^1$H NMR (600 MHz, CDCl$_3$) δ 9.80 (br s, 1H), 8.01 (br s, 1H), 7.38 (d, J=7.9 Hz, 1H), 7.24-7.20 (m, 1H), 7.18-7.09 (m, 2H), 6.93 (d, J=8.7 Hz, 2H), 6.88 (d, J=8.9 Hz, 2H), 6.39 (s, 1H), 6.34 (s, 1H), 6.08 (s, 1H), 5.88 (dd, J=10.0, 4.7 Hz, 1H), 5.41 (s, 1H), 5.30 (d, J=10.1 Hz, 1H), 4.60 (d, J=12.0 Hz, 1H), 4.04 (t, J=12.0 Hz, 1H), 3.82 (s, 3H), 3.80 (s, 3H), 3.79 (s, 3H), 3.77 (s, 3H), 3.66 (s, 3H), 3.65-3.58 (m, 2H), 3.52-3.48 (m, 1H), 3.38-3.33 (m, 2H), 3.31-3.27 (m, 1H), 3.02-2.93 (m, 2H), 2.86-2.79 (m, 2H), 2.73 (s, 3H), 2.66 (s, 1H), 2.48-2.41 (m, 1H), 2.18-2.14 (m, 2H), 2.11 (s, 3H), 2.04-1.97 (m, 1H), 1.83-1.74 (m, 2H), 1.35-1.28 (m, 2H), 0.87 (t, J=7.3 Hz, 3H), 0.79 (t, J=7.3 Hz, 3H); IR (film) $\nu_{max}$ 3447, 2899, 1742, 1507, 1459, 1234, 1036, 736 cm$^{-1}$; HRESI-TOF m/z 959.4917 ($C_{54}H_{66}N_6O_{10}$+H$^+$, required 959.4913); $[\alpha]_D^{23}$−9.4 (c 0.04, CHCl$_3$).

Compound (R=20'-NHCONH(3-methoxyphenyl)) 29

Yield: 50%, Method 1. $^1$H NMR (600 MHz, CDCl$_3$) δ 9.82 (br s, 1H), 7.96 (br s, 1H), 7.47 (d, J=7.9 Hz, 1H), 7.19 (t, J=8.1 Hz, 1H), 7.16-7.13 (m, 1H), 7.12-7.06 (m, 3H), 6.99 (d, J=8.6 Hz, 1H), 6.62 (s, 1H), 6.61 (d, J=8.1 Hz, 1H), 6.08 (s, 1H), 5.85 (dd, J=10.2, 4.6 Hz, 1H), 5.46 (s, 1H), 5.30 (d, J=9.9 Hz, 1H), 4.82 (s, 1H), 3.79 (s, 6H), 3.78 (s, 3H), 3.74 (s, 1H), 3.66-3.62 (m, 3H), 3.59 (s, 3H), 3.38-3.35 (m, 2H), 3.31-3.27 (m, 1H), 3.22-3.18 (m, 1H), 3.15-3.10 (m, 1H), 3.03 (d, J=13.3 Hz, 2H), 2.82 (d, J=16.1 Hz, 1H), 2.71 (s, 3H), 2.66 (s, 1H), 2.58 (d, J=13.8 Hz, 1H), 2.47-2.40 (m, 1H), 2.34 (d, J=13.0 Hz, 1H), 2.22-2.14 (m, 2H), 2.10 (s, 3H), 1.84-1.76 (m, 3H), 1.75-1.69 (m, 2H), 1.38-1.31 (m, 2H), 1.23-1.21 (m, 1H), 0.81 (ovlp t, J=7.4 Hz, 3H), 0.80 (ovlp t, J=7.4 Hz, 3H); IR (film) $\nu_{max}$ 3483, 2985, 1745, 1501, 1454, 1228, 1033, 760 cm$^{-1}$; HRESI-TOF m/z 959.4905 ($C_{54}H_{66}N_6O_{10}$+H$^+$, required 959.4913); $[\alpha]_D^{23}$−19 (c 0.05, CHCl$_3$).

Compound (R=20'-NHCONH(2-methoxyphenyl)) 30

Yield: 35%, Method 1. $^1$H NMR (600 MHz, CDCl$_3$) δ 9.85 (br s, 1H), 8.07 (d, J=9.1 Hz, 1H), 8.01 (br s, 1H), 7.49 (d, J=7.9 Hz, 1H), 7.17-7.12 (m, 1H), 7.13-7.07 (m, 2H), 7.05-6.95 (m, 2H), 6.88-6.86 (m, 1H), 6.64 (s, 1H), 6.10 (s, 1H), 5.85 (dd, J=10.0, 4.7 Hz, 1H), 5.47 (s, 1H), 5.30 (d, J=10.1 Hz, 1H), 5.13-5.10 (m, 1H), 4.76 (br s, 1H), 4.57 (br s, 1H), 3.85 (s, 3H), 3.80 (s, 3H), 3.80 (s, 3H), 3.74 (s, 1H), 3.56 (s, 3H), 3.40-3.36 (m, 2H), 3.34-3.20 (m, 2H), 3.14-3.07 (m, 2H), 2.71 (s, 3H), 2.67 (s, 1H), 2.60 (d, J=13.7 Hz, 1H), 2.50-2.42 (m, 1H), 2.39 (d, J=12.9 Hz, 1H), 2.27 (d, J=13.7 Hz, 1H), 2.20-2.15 (m, 2H), 2.11 (s, 3H), 2.09-1.99 (m, 2H), 1.84-1.76 (m, 4H), 1.50-1.39 (m, 2H), 1.38-1.28 (m, 2H), 0.81 (ovlp t, J=7.4 Hz, 3H), 0.80 (ovlp t, J=7.4 Hz, 3H); IR (film) $\nu_{max}$ 3451, 2919, 1730, 1531, 1461, 1257, 952, 721 cm$^{-1}$; HRESI-TOF m/z 959.4909 ($C_{54}H_{66}N_6O_{10}$+H$^+$, required 959.4913); $[\alpha]_D^{23}$+24 (c 0.03, CHCl$_3$).

Compound (R=20'-NHCONHCH$_2$C$_6$H$_5$) 31

Yield: 96%, Method 1. $^1$H NMR (600 MHz, CDCl$_3$) δ 9.84 (br s, 1H), 7.98 (br s, 1H), 7.47 (d, J=8.1 Hz, 1H), 7.45 (d, J=8.0 Hz, 2H), 7.31 (t, J=7.8 Hz, 2H), 7.17-7.08 (m, 4H), 6.62 (s, 1H), 6.09 (s, 1H), 5.85 (dd, J=10.3, 4.6 Hz, 1H), 5.47 (s, 1H), 5.30 (d, J=9.4 Hz, 1H), 4.68 (s, 1H), 4.48-4.31 (m, 2H), 3.80 (s, 3H), 3.79 (s, 3H), 3.74 (s, 1H), 3.60 (s, 3H), 3.38-3.33 (m, 2H), 3.31-3.26 (m, 1H), 3.22-3.18 (m, 1H), 3.10 (s, 3H), 2.83 (d, J 16.3 Hz, 1H), 2.70 (s, 3H), 2.67 (s, 1H), 2.59 (d, J=13.8 Hz, 1H), 2.47-2.42 (m, 1H), 2.36-2.28 (m, 2H), 2.25-2.13 (m, 2H), 2.11 (s, 3H), 2.04 (s, 1H), 1.83-1.71 (m, 3H), 1.71-1.65 (m, 2H), 1.64-1.54 (m, 2H), 1.24-1.20 (m, 2H), 0.83 (t, J=7.4 Hz, 3H), 0.80 (t, J=7.4 Hz, 3H); IR (film) $\nu_{max}$ 3454, 2992, 1737, 1501, 1459, 1231, 1033, 729 cm$^{-1}$; HRESI-TOF m/z 943.4950 ($C_{54}H_{66}N_6O_9$+H$^+$, required 943.4964); $[\alpha]_D^{23}$+29 (c 0.3, CHCl$_3$).

Compound (R=20'-NHCONHCH$_2$CH$_2$C$_6$H$_5$) 32

Yield: 98%, Method 1. $^1$H NMR (600 MHz, CDCl$_3$) δ 9.83 (br s, 1H), 7.97 (br s, 1H), 7.40 (d, J=8.1 Hz, 1H), 7.31 (t, J=7.8 Hz, 2H), 7.17-7.08 (m, 6H), 6.39 (s, 1H), 6.07 (s, 1H), 5.89 (dd, J 10.3, 4.6 Hz, 1H), 5.39 (s, 1H), 5.32 (d, J=9.4 Hz, 1H), 4.52 (s, 1H), 3.80 (s, 3H), 3.78 (s, 3H), 3.74 (s, 1H), 3.65 (s, 3H), 3.64-3.63 (m, 2H), 3.49-3.43 (m, 1H), 3.37-3.32 (m, 1H), 3.31-3.19 (m, 1H), 3.10 (s, 3H), 2.99 (d, J=15 Hz, 1H), 2.95-2.89 (m, 2H), 2.72 (s, 3H), 2.67 (s, 1H), 2.58-2.50 (m, 1H), 2.45-2.37 (m, 1H), 2.40-2.30 (m, 2H), 2.25-2.13 (m, 2H), 2.11 (s, 3H), 2.00-1.94 (m, 1H), 1.84-1.70 (m, 4H), 1.71-1.65 (m, 2H), 1.64-1.54 (m, 2H), 1.34-1.28 (m, 2H), 0.87 (t, J=7.4 Hz, 3H), 0.83 (t, J=7.4 Hz, 3H); IR (film) $\nu_{max}$ 3448, 2927, 1742, 1555, 1461, 1236, 1038, 749 cm$^{-1}$; HRESI-TOF m/z 957.5106 ($C_{55}H_{68}N_6O_9$+H$^+$, required 957.5121); $[\alpha]_D^{23}$−17 (c 0.06, CHCl$_3$).

Compound (R=20'-NHCONHCH$_2$(2-pyridyl)) 33

Yield: 79%, Method 2. $^1$H NMR (600 MHz, CDCl$_3$) δ 9.84 (br s, 1H), 8.52 (s, 1H), 8.04 (br s, 1H), 7.66 (t, J=8.1 Hz, 1H), 7.48 (d, J=7.9 Hz, 1H), 7.39 (d, J=7.7 Hz, 1H), 7.18-7.08 (m, 3H), 6.67 (s, 1H), 6.09 (s, 1H), 5.87-5.83 (m, 1H), 5.54 (br s, 1H), 5.47 (s, 1H), 5.30 (d, J=10.4 Hz, 1H), 4.62-4.52 (m, 2H), 3.87-3.83 (m, 1H), 3.80 (s, 6H), 3.74 (s, 1H), 3.57 (s, 3H), 3.39-3.28 (m, 3H), 3.23-3.17 (m, 1H), 3.10-3.02 (m, 1H), 2.83 (d, J=15.0 Hz, 1H), 2.71 (s, 3H), 2.67 (s, 1H), 2.57 (d, J=13.8 Hz, 1H), 2.48 (q, J=9.5 Hz, 1H), 2.35 (d, J=14.6 Hz, 1H), 2.28 (d, J=9.8 Hz, 1H), 2.21-2.16 (m, 1H), 2.11 (s, 3H), 1.99 (s, 1H), 1.45-1.32 (m, 1H), 1.86-1.70 (m, 8H), 1.27-1.22 (m, 2H), 0.80 (t, J=6.8 Hz, 3H), 0.73 (t, J=7.1 Hz, 3H); IR (film) $\nu_{max}$ 3375, 2925, 1737, 1503, 1459, 1230, 1039 cm$^{-1}$; HRESI-TOF m/z 944.4913 ($C_{53}H_{65}N_7O_9$+H$^+$, required 944.4916); $[\alpha]_D^{23}$+2.7 (c 0.2, CHCl$_3$).

Compound (R=20'-NHCONHCH$_2$(2-furyl)) 34

Yield: 96%, Method 1. $^1$H NMR (600 MHz, CDCl$_3$) δ 9.83 (br s, 1H), 7.98 (br s, 1H), 7.50 (d, J=8.2 Hz, 1H), 7.35 (s, 1H), 7.17-7.08 (m, 3H), 6.66 (s, 1H), 6.31 (d, J=9.0 Hz, 2H), 6.21 (br s, 1H) 6.09 (s, 1H), 5.86 (dd, J=9.8, 4.7 Hz, 1H), 5.47 (s, 1H), 5.30 (d, J=10.0 Hz, 1H), 4.40-4.37 (m, 2H), 3.80 (s, 6H), 3.74 (s, 1H), 3.59 (s, 3H), 3.40-3.28 (m, 2H), 3.26-3.20 (m, 1H), 3.22-3.18 (m, 1H), 3.10-3.00 (m, 3H), 2.83 (d, J=17.3 Hz, 1H), 2.71 (s, 3H), 2.67 (s, 1H), 2.55 (d, J=14.2 Hz, 1H), 2.47-2.42 (m, 1H), 2.35 (d, J=12.8 Hz, 1H), 2.25-2.15 (m, 1H), 2.11 (s, 3H), 2.02 (s, 1H), 1.85-1.76 (m, 3H), 1.71-1.65 (m, 4H), 1.37-1.20 (m, 4H), 0.81 (t, J=7.4 Hz, 3H), 0.72 (t, J=7.5 Hz, 3H); IR (film) $\nu_{max}$ 3388, 2925, 1739, 1504, 1459, 1230, 1039 cm$^{-1}$; HRESI-TOF m/z 933.4736 (C$_{52}$H$_{64}$N$_6$O$_{10}$+H$^+$, required 933.4756); [α]$_D^{23}$+11 (c 0.1, CHCl$_3$).

Compound (R=20'-NHCONH(4-biphenyl)) 35

Yield: 44%, Method 1. $^1$H NMR (600 MHz, CDCl$_3$) δ 9.82 (br s, 1H), 7.98 (br s, 1H), 7.58-7.51 (m, 6H), 7.45 (d, J=8.0 Hz, 1H), 7.41 (t, J=7.6 Hz, 2H), 7.31 (t, J=7.4 Hz, 1H), 7.17-7.13 (m, 1H), 7.13-7.06 (m, 2H), 6.64 (s, 1H), 6.09 (s, 1H), 5.86 (dd, J=10.4, 4.8 Hz, 1H), 5.47 (s, 1H), 5.31 (d, J=10.2 Hz, 1H), 4.82 (br s, 1H), 3.82 (t, J=13.8 Hz, 1H), 3.80 (s, 3H), 3.79 (s, 3H), 3.75 (s, 1H), 3.61 (s, 3H), 3.39-3.36 (m, 2H), 3.32-3.28 (m, 1H), 3.19 (t, J=11.4 Hz, 1H), 3.14-3.06 (m, 1H), 3.02 (d, J=12.5 Hz, 2H), 2.82 (d, J=15.7 Hz, 1H), 2.71 (s, 3H), 2.67 (s, 3H), 2.60 (d, J=13.8 Hz, 2H), 2.47-2.42 (m, 1H), 2.35 (d, J=13.0 Hz, 1H), 2.23 (d, J=14.2 Hz, 1H), 2.21-2.14 (m, 1H), 2.11 (s, 3H), 1.82-1.77 (m, 4H), 1.73-1.65 (m, 4H), 1.37-1.34 (m, 1H), 0.82 (t, J=7.4 Hz, 6H); IR (film) ν$_{max}$ 3444, 2967, 1735, 1523, 1459, 1240, 1039, 744 cm$^{-1}$; HRESI-TOF m/z 1005.5122 (C$_{59}$H$_{68}$N$_6$O$_9$+H$^+$, required 1005.5121); [α]$_D^{23}$-8.8 (c 0.1, CHCl$_3$).

Compound (R=20'-NHCSNHC$_6$H$_{11}$) 36

Yield: 26%, Method 4. $^1$H NMR (600 MHz, CDCl$_3$) δ 9.85 (br s, 1H), 8.03 (br s, 1H), 7.51 (d, J=7.7 Hz, 1H), 7.16-7.14 (m, J=7.0 Hz, 1H), 7.12-7.06 (m, 2H), 6.62 (s, 1H), 6.10 (s, 1H), 5.84 (dd, J=10.1, 4.1 Hz, 1H), 5.47 (s, 2H), 5.35-5.33 (m, 1H), 5.29 (d, J=9.1 Hz, 1H), 3.79 (s, 3H), 3.78 (s, 3H), 3.73 (s, 1H), 3.67-3.63 (m, 2H), 3.60 (s, 3H), 3.44 (s, 1H), 3.39-3.33 (m, 2H), 3.32-3.26 (m, 1H), 3.24-3.14 (m, 2H), 3.09 (q, J=7.7 Hz, 1H), 2.81 (d, J=14.7 Hz, 1H), 2.70 (s, 3H), 2.65 (s, 1H), 2.62-2.60 (m, 1H), 2.47-2.42 (m, 1H), 2.38-2.26 (m, 3H), 2.24-2.14 (m, 3H), 2.10 (s, 3H), 2.08-1.97 (m, 5H), 1.83-1.66 (m, 4H), 1.44-1.36 (m, 4H), 1.20-1.06 (m, 2H), 0.87 (t, J=6.9 Hz, 3H), 0.81 (t, J=6.9 Hz, 3H); IR (film) ν$_{max}$ 3467, 2912, 1727, 1506, 1456, 1230, 1087, 774 cm$^{-1}$; HRESI-TOF m/z 951.5051 (C$_{53}$H$_{70}$N$_6$O$_8$S+H$^+$, required 951.5048); [α]$_D^{23}$+9.2 (c 0.2, CHCl$_3$).

Compound (R=20'-NHCSNHC$_6$H$_5$) 37

Yield: 70%, Method 3. $^1$H NMR (500 MHz, CDCl$_3$) δ 9.82 (br s, 1H), 8.09 (br s, 1H), 7.54 (m, 4H), 7.49 (d, J=8.0 Hz, 1H), 7.40 (t, J=7.2 Hz, 1H), 7.24-7.19 (m, 1H), 7.19-7.14 (m, 2H), 6.60 (s, 1H), 6.25 (s, 1H), 6.18 (s, 1H), 5.92 (dd, J=10.0, 4.3 Hz, 1H), 5.56 (s, 1H), 5.37 (d, J=10.0 Hz, 1H), 3.89 (s, 3H), 3.88 (s, 3H), 3.80 (s, 3H), 3.70 (s, 3H), 3.49-3.32 (m, 4H), 3.17-3.07 (m, 2H), 2.94-2.80 (m, 3H), 2.78 (s, 3H), 2.65-3.62 (m, 1H), 2.52-2.43 (m, 1H), 2.33-2.22 (m, 4H), 2.19 (s, 3H), 1.94-1.80 (m, 2H), 1.44-1.37 (m, 3H), 1.14 (d, J=9.2 Hz, 1H), 0.88 (t, J=6.3 Hz, 6H); IR (film) ν$_{max}$ 3449, 2930, 1737, 1498, 1458, 1231, 1039, 751 cm$^{-1}$; HRESI-TOF m/z 945.4573 (C$_{53}$H$_{64}$N$_6$O$_8$S+H$^+$, required 945.4579); [α]$_D^{23}$+8.1 (c 0.2, CHCl$_3$).

Compound (R=20'-NHCSNHCH$_2$CH$_2$ (4-fluorophenyl)) 38

Yield: 91%, Method 4. $^1$H NMR (600 MHz, CDCl$_3$) δ 9.83 (br s, 1H), 8.01 (br s, 1H), 7.51 (d, J=8.8 Hz, 1H), 7.26-7.24 (m, 2H), 7.17-7.08 (m, 3H), 6.97-6.94 (m, 2H), 6.64 (s, 1H), 6.12 (s, 1H), 5.85 (dd, J=10.1, 3.4 Hz, 1H), 5.75 (br s, 1H), 5.48 (s, 1H), 5.30 (d, J=10.2 Hz, 1H), 3.80 (s, 3H), 3.79 (s, 3H), 3.77-3.74 (m, 3H), 3.61 (s, 3H), 3.60 (s, 1H), 3.42-3.35 (m, 2H), 3.32-3.28 (m, 1H), 3.25-3.10 (m, 3H), 3.02-2.97 (m, 1H), 2.96-2.91 (m, 1H), 2.83-2.80 (m, 1H), 2.72 (s, 3H), 2.66 (s, 1H), 2.55 (d, J=13.7 Hz, 1H), 2.47-2.42 (m, 1H), 2.32 (d, J=13.8 Hz, 1H), 2.22-2.17 (m, 2H), 2.11 (s, 3H), 1.84-1.65 (m, 4H), 1.54-1.44 (m, 2H), 1.37-1.22 (m, 5H), 0.82 (t, J=7.2 Hz, 3H), 0.74 (t, J=7.4 Hz, 3H); IR (film) ν$_{max}$ 3468, 2961, 1737, 1507, 1461, 1226, 1038 cm$^{-1}$; HRESI-TOF m/z 991.4790 (C$_{55}$H$_{67}$N$_6$O$_8$S+H$^+$, required 991.4798); [α]$_D^{23}$+6.6 (c 0.2, CHCl$_3$).

Compound (R=20'-NHCON(CH$_3$)$_2$) 39

Yield: 99%, Method 2. $^1$H NMR (600 MHz, CDCl$_3$) δ 9.84 (br s, 1H), 7.98 (br s, 1H), 7.48 (d, J=8.2 Hz, 1H), 7.17-7.13 (m, 1H), 7.12-7.07 (m, 2H), 6.62 (s, 1H), 6.09 (s, 1H), 5.86 (dd, J=10.0, 5.1 Hz, 1H), 5.46 (s, 1H), 5.30 (d, J=10.3 Hz, 1H), 4.68 (s, 1H), 3.90 (t, J=14.7 Hz, 1H), 3.79 (s, 3H), 3.79 (s, 3H), 3.73 (s, 1H), 3.58 (s, 3H), 3.38-3.35 (m, 2H), 3.31-3.27 (m, 2H), 3.23-3.19 (m, 2H), 3.17-3.12 (m, 2H), 3.05 (s, 6H), 2.82 (d, J=16.0 Hz, 1H), 2.70 (s, 3H), 2.67 (s, 1H), 2.58 (d, J=13.9 Hz, 1H), 2.47-2.42 (m, 1H), 2.38 (d, J=13.1 Hz, 1H), 2.23-2.14 (m, 2H), 2.10 (s, 1H), 1.87-1.74 (m, 4H), 1.69 (d, J=13.9 Hz, 2H), 1.40-1.33 (m, 4H), 0.81 (t, J=7.4 Hz, 3H), 0.75 (t, J=7.4 Hz, 3H); IR (film) ν$_{max}$ 3472, 2955, 1723, 1500, 1459, 1258, 1038, 777 cm$^{-1}$; HRESI-TOF m/z 881.4790 (C$_{49}$H$_{64}$N$_6$O$_9$+H$^+$, required 881.4808); [α]$_D^{23}$-50 (c 0.04, CHCl$_3$).

Compound (R=20'-NHCON(CH$_2$CH$_3$)$_2$) 40

Yield: 88%, Method 2. $^1$H NMR (600 MHz, CDCl$_3$) δ 9.87 (br s, 1H), 8.02 (br s, 1H), 7.51 (d, J=7.8 Hz, 1H), 7.18-7.13 (m, 1H), 7.13-7.07 (m, 2H), 6.62 (s, 1H), 6.10 (s, 1H), 5.85 (dd, J=10.2, 4.1 Hz, 1H), 5.47 (s, 1H), 5.30 (d, J=10.2 Hz, 1H), 4.35 (br s, 1H), 3.85 (t, J=12.7 Hz, 2H), 3.79 (s, 6H), 3.74 (s, 1H), 3.59 (s, 3H), 3.51-3.45 (m, 1H), 3.40-3.20 (m, 3H), 3.17-3.12 (m, 1H), 2.83 (d, J=16.2 Hz, 1H), 2.71 (s, 7H), 2.58 (d, J=13.7 Hz, 1H), 2.47-2.42 (m, 1H), 2.39 (d, J=12.7 Hz, 1H), 2.23 (d, J=14.4 Hz, 1H), 2.20-2.14 (m, 2H), 2.11 (s, 3H), 2.08 (s, 1H), 1.88-1.67 (m, 4H), 1.37-1.32 (m, 1H), 1.29-1.25 (m, 4H), 1.23 (t, J=7.1 Hz, 6H), 0.81 (t, J=7.3 Hz, 3H), 0.75 (t, J=7.4 Hz, 3H); IR (film) ν$_{max}$ 3486, 2940, 1741, 1520, 1458, 1233, 1042, 709 cm$^{-1}$; HRESI-TOF m/z 909.5130 (C$_{51}$H$_{68}$N$_6$O$_9$+H$^+$, required 909.5121); [α]$_D^{23}$-38 (c 0.08, CHCl$_3$).

Compound (R=20'-NHCO-(morpholine)) 41

Yield: 99%, Method 2. $^1$H NMR (600 MHz, CDCl$_3$) δ 9.84 (br s, 1H), 8.06 (s, 1H), 7.99 (br s, 1H), 7.51 (d, J=7.8 Hz, 1H), 7.19-7.14 (m, 1H), 7.13-7.07 (m, 2H), 6.62 (s, 1H), 6.10 (s, 1H), 5.85 (dd, J=10.1, 4.1 Hz, 1H), 5.47 (s, 1H), 5.30 (d, J=10.1 Hz, 1H), 4.48 (s, 1H), 3.85 (d, J=10.9 Hz, 3H), 3.80 (s, 3H), 3.80 (s, 3H), 3.79-3.77 (m, 1H), 3.77-3.64 (m, 11H), 3.62-3.56 (m, 4H), 3.48-3.44 (m, 1H), 3.38-3.36 (m, 1H), 3.33-3.05 (m, 2H), 2.83 (d, J=16.1 Hz, 1H), 2.71 (s, 3H), 2.67 (s, 1H), 2.60 (d, J=13.6 Hz, 1H), 2.47-2.42 (m, 1H), 2.40 (d, J=12.5 Hz, 1H), 2.29-2.22 (m, 2H), 2.20-2.15 (m, 2H), 2.11 (s, 3H), 1.90-1.74 (m, 2H), 1.70-1.67 (m, 2H), 1.37-1.32 (m, 2H), 0.81 (t, J=7.3 Hz, 3H), 0.76 (t, J=7.5 Hz, 3H); IR (film) ν$_{max}$ 3448, 2919, 1740, 1538, 1449, 1247, 1032, 711 cm$^{-1}$; HRESI-TOF m/z 923.4897 (C$_{51}$H$_{66}$N$_6$O$_{10}$+H$^+$, required 923.4913); [α]$_D^{23}$-8.0 (c 0.1, CHCl$_3$).

Compound (R=20'-NHCO-(piperidine)) 42

Yield: 34%, Method 2. $^1$H NMR (600 MHz, CDCl$_3$) δ 9.85 (br s, 1H), 8.02 (br s, 1H), 7.50 (d, J=7.4 Hz, 1H), 7.17-7.14 (m, 1H), 7.11-7.09 (m, 2H), 6.59 (s, 1H), 6.09 (s, 1H), 5.84 (dd, J=10.1, 4.1 Hz, 1H), 5.45 (s, 1H), 5.29 (d, J=10.4 Hz, 1H), 4.45 (s, 1H), 3.82 (t, J=14.7 Hz, 1H), 3.80 (s, 3H), 3.79 (s, 3H), 3.73 (s, 1H), 3.59 (s, 3H), 3.52-3.48 (m, 2H), 3.43-3.40 (m, 2H), 3.38-3.34 (m, 2H), 3.31-3.26 (m, 4H), 3.18-3.12 (m, 2H), 2.82 (d, J=16.6 Hz, 1H), 2.70 (s, 3H), 2.66 (s, 1H), 2.47-2.38 (m, 4H), 2.28-2.20 (m, 2H), 2.18-2.14 (m, 2H), 2.10 (s, 3H), 2.07 (s, 1H), 1.90-1.76 (m, 4H), 1.69 (s, 1H), 1.35-1.27 (m, 5H), 0.80 (t, J=7.3 Hz, 3H), 0.75 (t, J=7.3 Hz, 3H); IR (film) ν$_{max}$ 3458, 2958, 1791, 1509, 1466, 1251, 1061, 737 cm$^{-1}$; HRESI-TOF m/z 921.5103 (C$_{52}$H$_{68}$N$_6$O$_9$+H$^+$, required 921.5121); [α]$_D^{23}$ 9.2 (c 0.02, CHCl$_3$).

Compound (R=20'-NHCSN(CH$_3$)$_2$) 43

Yield: 71%, Method 4. $^1$H NMR (600 MHz, CDCl$_3$) δ 9.83 (br s, 1H), 7.98 (br s, 1H), 7.50 (d, J=7.8 Hz, 1H), 7.18-7.13 (m, 1H), 7.12-7.08 (m, 2H), 6.64 (d, J=3.9 Hz, 1H), 6.10 (s, 1H), 5.86 (dd, J=10.0, 5.1 Hz, 1H), 5.54 (s, 1H), 5.47 (s, 1H), 5.31 (d, J=10.0 Hz, 1H), 4.70-4.67 (m, 1H), 3.81 (s, 3H), 3.80 (s, 3H), 3.75 (s, 1H), 3.59 (s, 3H), 3.44 (s, 6H), 3.38 (d, J=12.2 Hz, 2H), 3.31 (d, J=4.7 Hz, 1H), 3.27-3.15 (m, 3H), 3.14-3.03 (m, 2H), 2.83 (d, J=15.2 Hz, 1H), 2.72 (s, 3H), 2.70 (s, 1H), 2.67 (s, 1H), 2.54 (d, J=13.7 Hz, 1H), 2.48-2.43 (m, 1H), 2.38 (d, J=14.1 Hz, 1H), 2.23-2.16 (m, 2H), 2.11 (s, 3H), 1.96 (d, J=15.2 Hz, 1H), 1.85-1.74 (m, 2H), 1.38-1.29 (m, 4H), 0.81 (t, J=7.4 Hz, 3H), 0.75 (t, J=7.4 Hz, 3H); IR (film) $v_{max}$ 3458, 2963, 1728, 1536, 1474, 1235, 1061, 737 cm$^{-1}$; HRESI-TOF m/z 897.4559 ($C_{49}H_{64}N_6O_8S+H^+$, required 897.4579); $[\alpha]_D^{23}$−56 (c 0.07, CHCl$_3$).

Compound (R=20'-OCON(CH$_3$)$_2$) 44

Yield: 88%. $^1$H NMR (600 MHz, CDCl$_3$) δ 9.86 (br s, 1H), 8.02 (br s, 1H), 7.50 (d, J=7.8 Hz, 1H), 7.17-7.12 (m, 1H), 7.12-7.07 (m, 2H), 6.61 (s, 1H), 6.09 (s, 1H), 5.84 (dd, J=10.2, 4.1 Hz, 1H), 5.46 (s, 1H), 5.29 (d, J=10.0 Hz, 1H), 4.34 (s, 1H), 3.84 (t, J=12.7 Hz, 1H), 3.79 (s, 6H), 3.74 (s, 1H), 3.58 (s, 3H), 3.47 (dd, J=14.6, 7.2 Hz, 2H), 3.40-3.19 (m, 4H), 3.16-3.12 (m, 2H), 2.82 (d, J=16.2 Hz, 1H), 2.70 (s, 9H), 2.66 (s, 1H), 2.57 (d, J=13.7 Hz, 1H), 2.46-2.41 (m, 1H), 2.38 (d, J=12.7 Hz, 1H), 2.22 (d, J=14.4 Hz, 1H), 2.20-2.13 (m, 1H), 2.10 (s, 3H), 2.07 (s, 1H), 1.86-1.76 (m, 2H), 1.72 (d, J=14.5 Hz, 2H), 1.38-1.30 (m, 2H), 0.80 (t, J=7.3 Hz, 3H), 0.75 (t, J=7.4 Hz, 3H); IR (film) $v_{max}$ 3472, 2969, 1731, 1539, 1459, 1224, 1048, 740 cm$^{-1}$; HRESI-TOF m/z 882.4642 ($C_{49}H_{63}N_5O_{10}+H^+$, required 882.4648); $[\alpha]_D^{23}$−64 (c 0.03, CHCl$_3$).

Compound (R=20'-NHCH$_3$) 45

A solution 20'-aminovinblastine (8.8 mg, 0.011 mmol) in THF (3 mL) was treated with a 37% formaldehyde in water solution (4 μL, 0.05 mmol). The reaction mixture was stirred for 4 h at 25° C. and then was treated with sodium cyanoborohydride (12 mg, 0.20 mmol). The reaction mixture was stirred for 1 h at 25° C. and then was quenched with distilled H$_2$O (3 mL). The mixture was extracted with 10% MeOH in CH$_2$Cl$_2$, and the combined organic extracts were washed with saturated aqueous NaCl (3 mL). The organic layer was dried over Na$_2$SO$_4$, and concentrated under reduced pressure. PTLC (SiO$_2$, EtOAc:MeOH:Et$_3$N=97:3:3) provided 45 (2.8 mg, 32%, off white solid) and 46 (2.9 mg, 33%, off white solid). For 45: $^1$H NMR (600 MHz, CDCl$_3$) δ 9.87 (br s, 1H), 8.01 (br s, 1H), 7.51 (d, J=7.5 Hz, 1H), 7.18-7.14 (m, 1H), 7.11-7.08 (m, 2H), 6.58 (br s, 1H), 6.09 (s, 1H), 5.85 (dd, J=9.9, 4.0 Hz, 1H), 5.46 (s, 1H), 5.30 (d, J=9.8 Hz, 1H), 4.07-3.91 (m, 2H), 3.80 (s, 3H), 3.79 (s, 3H), 3.73 (s, 1H), 3.61 (s, 3H), 3.36 (dd, J=16.3, 4.6 Hz, 1H), 3.31-3.26 (m, 1H), 3.12-3.04 (m, 2H), 2.83 (d, J=16.1 Hz, 1H), 2.71 (s, 3H), 2.67 (s, 3H), 2.46-2.41 (m, 1H), 2.37-2.31 (m, 1H), 2.31-2.20 (m, 1H), 2.17-2.13 (m, 1H), 2.11 (s, 3H), 1.87-1.73 (m, 2H), 1.18-1.08 (m, 2H), 0.81 (t, J=7.4 Hz, 3H), 0.78 (t, J=7.4 Hz, 3H); IR (film) $v_{max}$ 3487, 2953, 1729, 1505, 1461, 1239, 1037, 735 cm$^{-1}$; HRESI-TOF m/z 824.4576 ($C_{47}H_{61}N_5O_8+H^+$, required 824.4593); $[\alpha]_D^{23}$−114 (c 0.03, CHCl$_3$).

Compound (R=20'-N(CH$_3$)$_2$) 46

$^1$H NMR (600 MHz, CDCl$_3$) δ 9.89 (br s, 1H), 7.98 (br s, 1H), 7.52 (d, J=7.7 Hz, 1H), 7.17-7.11 (m, 3H), 6.57 (br s, 1H), 6.10 (s, 1H), 5.85 (dd, J=9.5, 4.3 Hz, 1H), 5.46 (s, 1H), 5.30 (d, J=10.1 Hz, 1H), 3.97-3.92 (m, 1H), 3.80 (s, 3H), 3.79 (s, 3H), 3.73 (s, 1H), 3.61 (s, 3H), 3.38-3.27 (m, 4H), 3.20 (d, J=13.8 Hz, 1H), 3.17-3.12 (m, 1H), 2.84 (d, J=16.2 Hz, 1H), 2.71 (s, 3H), 2.67 (s, 3H), 2.46-2.41 (m, 1H), 2.38 (s, 6H), 2.31-2.29 (m, 1H), 2.18-2.14 (m, 1H), 2.11 (s, 3H), 1.87-1.73 (m, 6H), 1.49-1.42 (m, 2H), 1.36-1.31 (m, 2H), 0.83-0.78 (m, 6H); IR (film) $v_{max}$ 3404, 2951, 1734, 1501, 1459, 1227, 1037, 731 cm$^{-1}$; HRESI-TOF m/z 838.4752 ($C_{48}H_{63}N_5O_8+H^+$, required 838.4749); $[\alpha]_D^{23}$+16 (c 0.01, CHCl$_3$).

Compound (R=20'-NMeCONHCH$_2$CH$_3$) 47

Yield: 95%, Method 1. $^1$H NMR (600 MHz, CDCl$_3$) δ 9.83 (br s, 1H), 7.95 (br s, 1H), 7.51 (d, J=8.0 Hz, 1H), 7.16-7.09 (m, 3H), 6.66 (s, 1H), 6.08 (s, 1H), 5.86 (dd, J=9.9, 3.9 Hz, 1H), 5.48 (s, 1H), 5.31 (d, J=10.6 Hz, 1H), 4.54 (br s, 1H), 4.29 (br s, 1H), 3.80 (s, 3H), 3.77 (s, 3H), 3.74 (s, 1H), 3.70-3.65 (m, 1H), 3.57 (s, 3H), 3.43-3.37 (m, 2H), 3.33-3.18 (m, 5H),), 3.05-3.02 (m, 2H), 2.98 (br s, 3H), 2.82 (d, J=16.1 Hz, 1H), 2.71 (s, 3H), 2.67 (s, 1H), 2.56 (d, J=14.2 Hz, 1H), 2.47-2.43 (m, 1H), 2.36 (d, J=11.6 Hz, 1H), 2.24-2.16 (m, 2H), 2.11 (s, 3H), 1.87-1.75 (m, 3H), 1.38-1.32 (m, 5H), 1.19 (t, J=7.2 Hz, 3H), 0.83 (t, J=7.4 Hz, 3H), 0.79 (t, J=7.3 Hz, 3H); IR (film) $v_{max}$ 3462, 3400, 2926, 1735, 1504, 1460, 1243, 1039 cm$^{-1}$; HRESI-TOF m/z 895.4956 ($C_{50}H_{66}N_6O_9H^+$, required 895.4964); $[\alpha]_D^{23}$+17 (c 0.1, CHCl$_3$).

Compound 49

Iron(III) chloride hexahydrate (55 mg, 0.21 mmol) was added to a solution of (−)-vindoline (19 mg, 0.041 mmol) and 10'-fluorocatharanthine [Gotoh et al., ACS Med. Chem. Lett. 2011, 2:948-952] (15 mg, 0.041 mmol) in CF$_3$CH$_2$OH (0.1 mL), aqueous 0.1 N HCl (1.0 mL) and H$_2$O (1.0 mL) at 23° C. under Ar. The reaction mixture was stirred for 2 hours at 23° C. Meanwhile, in a separate flask, a mixture of iron(III) oxalate hexahydrate (198 mg, 0.41 mmol) in degassed H$_2$O (40 mL) was cooled to 0° C. and placed under Ar. CsN$_3$ (215 mg, 1.23 mmol) was added to the mixture at 0° C., followed by the vindoline coupling solution and NaBH$_4$ (31 mg, 0.81 mmol) in H$_2$O (1 mL). The resulting mixture was stirred for 30 minutes before being quenched by addition of 28-30% aqueous NH$_4$OH (4 mL).

The mixture was extracted with 10% MeOH in CH$_2$Cl$_2$, the organic layer was dried over Na$_2$SO$_4$, and concentrated under reduced pressure. PTLC (SiO$_2$, EtOAc:MeOH:Et$_3$N=97:3:3) provided 10'-fluoro-20'-azidovinblastine (50, 2.4 mg, 7%, white solid), and 10'-fluoro-20'-azidoleurosidine (6.0 mg, 17%, white solid). A solution of compound 50 (2.4 mg, 0.0028 mmol) in THF/H$_2$O (1/1 mL) was treated with CoCl$_2$.6H$_2$O (35 mg, 0.15 mmol) followed by NaBH$_4$ (17 mg, 0.45 mmol). The reaction mixture was stirred for 2 hours before being quenched with the addition of saturated NaHCO$_3$ (1 mL).

The mixture was extracted with 10% MeOH in CH$_2$Cl$_2$, and washed with saturated aqueous NaCl (1 mL). The organic layer was dried over Na$_2$SO$_4$, and concentrated under reduced pressure. PTLC (SiO$_2$, EtOAc:MeOH=90:10) provided 10'-fluoro-20'-aminovinblastine (51, 1.6 mg, 70%, white solid). A solution 51 (1.6 mg, 0.0019 mmol) in THF (3 mL) was treated with ethyl isocyanate (2 μL 0.025 mmol). The reaction mixture was stirred for 4 hours at 25° C. and then was concentrated under reduced pressure. PTLC (SiO$_2$, CH$_2$Cl$_2$:MeOH=92:8) provided 49 (1.0 mg, 59%, white solid).

50: $^1$H NMR (600 MHz, CDCl$_3$) δ 9.76 (br s, 1H), 8.00 (br s, 1H), 7.39 (dd, J=8.8, 5.1 Hz, 1H), 6.86-6.82 (m, 1H), 6.76 (dd, J=9.6, 2.4 Hz, 1H), 6.56 (s, 1H), 6.10 (s, 1H), 5.86 (dd, J=10.3, 4.6 Hz, 1H), 5.48 (s, 1H), 5.29 (d, J=10.2 Hz, 1H), 3.93 (t, J=14.1 Hz, 1H), 3.82-3.76 (m, 1H), 3.80 (s, 6H), 3.72 (s, 1H), 3.63 (s, 3H), 3.40-3.33 (m, 2H), 3.30-3.25 (m, 2H), 3.13-3.07 (m, 1H), 2.95 (d, J=14.4 Hz, 1H), 2.83-2.73 (m, 3H), 2.69 (s, 3H), 2.66 (s, 1H), 2.62 (s, 1H), 2.43-2.40 (m, 2H), 2.25 (d, J=13.9 Hz, 1H), 2.18-2.14 (m, 1H), 2.10 (s, 3H), 2.07 (s, 1H), 1.85-1.77 (m, 2H), 1.63-1.52 (m, 2H), 1.47-1.41 (m, 2H), 0.93 (t, J=7.5 Hz, 3H), 0.78 (t, J 7.4 Hz, 3H); IR (film) $v_{max}$ 2925, 2109, 1734, 1614, 1460, 1228, 1038 cm$^{-1}$; HRESI-TOF m/z 854.4218 ($C_{46}H_{56}FN_7O_8+H^+$, required 854.4247); $[\alpha]_D^{23}$−6.0 (c 0.08, CHCl$_3$).

51: $^1$H NMR (600 MHz, CDCl$_3$) δ 9.81 (br s, 1H), 8.00 (br s, 1H), 7.40-7.37 (m, 1H), 6.89-6.85 (m, 1H), 6.78 (d, J=9.2 Hz, 1H), 6.51 (s, 1H), 6.10 (s, 1H), 5.89 (dd, J=10.1, 4.0 Hz, 1H), 5.45 (s, 1H), 5.31 (d, J=10.1 Hz, 1H), 3.92 (t, J=14 Hz, 1H), 3.82-3.77 (m, 1H), 3.81 (s, 3H), 3.74 (s, 1H), 3.63 (s, 3H), 3.38 (d, J=16.0, 4.7 Hz, 2H), 3.32-3.27 (m, 1H), 3.10-3.05 (m, 2H), 2.84 (d, J=15.7 Hz, 1H), 2.75-2.68 (m, 3H), 2.71 (s, 3H), 2.64 (s, 1H), 2.50-2.45 (m, 1H), 2.17 (d, J=3.4 Hz, 1H), 2.11 (s, 3H), 2.08 (s, 1H), 2.05 (s, 1H), 1.87-1.75 (s, 4H), 1.42-1.15 (m, 6H), 0.88 (t, J=7.4 Hz, 3H), 0.78 (t, J=7.3 Hz, 3H); HRESI-TOF m/z 828.4311 ($C_{46}H_{58}FN_5O_8+H^+$, required 828.4311); $[\alpha]_D^{23}$−23 (c 0.10, CHCl$_3$).

49: ¹H NMR (600 MHz, CDCl₃) δ 9.77 (br s, 1H), 7.95 (br s, 1H), 7.39 (dd, J=8.8, 5.2 Hz, 1H), 6.86 (t, J=9.4 Hz, 1H), 6.77 (d, J=9.3 Hz, 1H), 6.58 (s, 1H), 6.09 (s, 1H), 5.88 (dd, J=9.8, 4.6 Hz, 1H), 5.47 (s, 1H), 5.31 (d, J=11.4 Hz, 1H), 4.41 (br s, 1H), 4.21 (br s, 1H), 3.84-3.77 (m, 2H), 3.80 (s, 6H), 3.75 (s, 1H), 3.61 (s, 3H), 3.40 (dd, J=17.0, 5.2 Hz, 2H), 3.35-3.19 (m, 4H), 3.16-3.08 (m, 2H), 2.82 (d, J=14.9 Hz, 1H), 2.71 (s, 3H), 2.65 (s, 1H), 2.57 (d, J=14.1 Hz, 1H), 2.47-2.43 (m, 1H), 2.39 (d, J=12.8 Hz, 1H), 2.22-2.17 (m, 2H), 2.11 (s, 3H), 1.87-1.75 (m, 4H), 1.69 (d, J=14.6 Hz, 2H), 1.43-1.38 (m, 3H), 1.19 (t, J=7.1 Hz, 3H), 0.79 (t, J=7.4 Hz, 3H), 0.77 (t, J=7.4 Hz, 3H); HRESI-TOF m/z 899.4713 (C₄₉H₆₃FN₆O₉+H⁺, required 899.4713).

Compound (R=20'-NHCO-pyrrolidine) 52
Yield: 79%; Method 2. ¹H NMR (600 MHz, CDCl₃) δ 9.86 (br s, 1H), 8.00 (br s, 1H), 7.50 (d, J=7.9 Hz, 1H), 7.16-7.14 (m, 1H), 7.11-7.09 (m, 2H), 6.62 (s, 1H), 6.11 (s, 1H), 5.85 (dd, J=10.1, 4.2 Hz, 1H), 5.47 (s, 1H), 5.30 (d, J=10.1 Hz, 1H), 4.25 (s, 1H), 3.89 (q, J=12.0, 10.3 Hz 1H), 3.80 (s, 3H), 3.80 (s, 3H), 3.74 (s, 1H), 3.59 (s, 3H), 3.56-3.52 (m, 2H), 3.49-3.45 (m, 2H), 3.38-3.35 (m, 2H), 3.30 (td, J=9.4, 4.7 Hz, 1H), 3.27-3.13 (m, 4H), 3.07-3.00 (m, 2H), 2.83 (d, J=16.0 Hz, 1H), 2.71 (s, 3H), 2.67 (s, 1H), 2.59 (d, J=13.8 Hz, 1H), 2.49-2.39 (m, 2H), 2.23 (d, J=15.3 Hz, 1H), 2.20-2.15 (m, 1H), 2.11 (s, 3H), 1.97-1.93 (m, 4H), 1.87-1.77 (m, 2H), 1.70 (d, J=14.6 Hz, 1H), 1.38-1.32 (m, 4H), 0.81 (t, J=7.3 Hz, 3H), 0.77 (t, J=7.4 Hz, 3H); IR (film) ν_max 3461, 2927, 1737, 1227 cm⁻¹; HRESI-TOF m/z 907.4953 (C₅₁H₆₆N₆O₉+H⁺, required 907.4964); [α]_D²³ −8 (c 0.2, CHCl₃).

Compound (R=20'-NHCO-thiomorpholine) 53
Yield: 34%; Method 2. ¹H NMR (600 MHz, CDCl₃) δ 9.84 (br s, 1H), 8.01 (br s, 1H), 7.51 (d, J=7.9 Hz, 1H), 7.18-7.15 (m, 1H), 7.13-7.10 (m, 2H), 6.62 (s, 1H), 6.10 (s, 1H), 5.85 (dd, J=10.5, 4.6 Hz, 1H), 5.47 (s, 1H), 5.30 (d, J=10.4 Hz, 1H), 4.42 (s, 1H), 3.88-3.85 (m, 1H), 3.80 (s, 3H), 3.80 (s, 3H), 3.74 (s, 1H), 3.60 (s, 3H), 3.39-3.35 (m, 2H), 3.30 (td, J=9.4, 4.6 Hz, 1H), 3.24-3.19 (m, 3H), 3.13-3.11 (m, 1H), 2.83 (d, J=16.0 Hz, 1H), 2.71 (s, 3H), 2.69-2.68 (m, 4H), 2.67 (s, 1H), 2.60 (d, J=13.8 Hz, 1H), 2.48-2.43 (m, 1H), 2.39 (d, J=13.4 Hz, 1H), 2.22-2.15 (m, 2H), 2.11 (s, 3H), 1.84-1.78 (m, 4H), 1.75-1.72 (m, 3H), 1.36-1.33 (m, 4H), 1.29-1.26 (m, 2H), 0.81 (t, J=7.4 Hz, 3H), 0.74 (t, J 7.4 Hz, 3H); IR (film) ν_max 3468, 2924, 1735, 1502, 1458, 1293, 1227 cm⁻¹; HRESI-TOF m/z 939.4683 (C₅₁H₆₆N₆O₉S+H⁺, required 939.4685); [α]_D²³ −58 (c 0.05, CHCl₃).

Compound (R=20'-NHCO—N-methylpiperazine) 54
Yield: 77%; Method 2. ¹H NMR (600 MHz, CDCl₃) δ 9.85 (br s, 1H), 8.00 (br s, 1H), 7.51 (d, J=7.9 Hz, 1H), 7.17-7.15 (m, 1H), 7.12-7.09 (m, 2H), 6.62 (s, 1H), 6.09 (s, 1H), 5.85 (dd, J=10.2, 4.3 Hz, 1H), 5.47 (s, 1H), 5.30 (d, J=10.4 Hz, 1H), 4.46 (s, 1H), 3.85 (t, J=12.9 Hz, 1H), 3.80 (s, 3H), 3.80 (s, 3H), 3.74 (s, 1H), 3.65-3.62 (m, 2H), 3.60 (s, 3H), 3.51-3.48 (m, 2H), 3.39-3.34 (m, 2H), 3.30 (td, J=9.5, 4.8 Hz, 1H), 3.23 (d, J=11.8 Hz, 2H), 3.15-3.12 (m, 2H), 2.84-2.80 (m, 7H), 2.71 (s, 3H), 2.67 (s, 1H), 2.58 (d, J=13.8 Hz, 1H), 2.47-2.37 (m, 6H), 2.29 (s, 3H), 2.21-2.15 (m, 2H), 2.11 (s, 3H), 1.92-1.88 (m, 1H), 1.84-1.81 (m, 1H), 1.66 (d, J=14.4 Hz, 1H), 0.81 (t, J=7.4 Hz, 3H), 0.75 (t, J=7.4 Hz, 3H); IR (film) ν_max 3465, 2932, 1736, 1503, 1458, 1227, 1038 cm⁻¹; HRESI-TOF m/z 936.5226 (C₅₂H₆₉N₇O₉+H⁺, required 936.5229); [α]_D²³ −15 (c 0.2, CHCl₃).

Compound (R=20'-NHCO-1,2,5,6-tetrahydropyridine) 55
Yield: 71%; Method 2. ¹H NMR (600 MHz, CDCl₃) δ 9.86 (br s, 1H), 8.01 (br s, 1H), 7.50 (d, J=7.9 Hz, 1H), 7.17-7.14 (m, 1H), 7.11-7.08 (m, 2H), 6.62 (s, 1H), 6.10 (s, 1H), 5.87-5.84 (m, 1H), 5.85 (dd, J=10.2, 3.9 Hz, 1H), 5.73 (d, J=10.1 Hz, 1H), 5.47 (s, 1H), 5.30 (d, J=10.2 Hz, 1H), 4.46 (br s, 1H), 4.09-4.01 (m, 2H), 3.89-3.84 (m, 1H), 3.81 (s, 3H), 3.80 (s, 3H), 3.75-3.71 (m, 2H), 3.74 (s, 1H), 3.60 (s, 3H), 3.50-3.46 (m, 1H), 3.39-3.34 (m, 2H), 3.30 (td, J=9.4, 4.8 Hz, 1H), 3.22 (dd, J=11.9, 5.6 Hz, 1H), 3.13 (d, J=12.5 Hz, 2H), 2.83 (d, J=16.1 Hz, 1H), 2.71 (s, 3H), 2.67 (s, 1H), 2.59 (d, J=13.7 Hz, 1H), 2.47-2.42 (m, 1H), 2.40 (d, J=13.5 Hz, 1H), 2.24-2.15 (m, 4H), 2.11 (s, 3H), 1.89-1.69 (m, 4H), 1.35-1.25 (m, 5H), 0.81 (t, J=7.4 Hz, 3H), 0.75 (t, J=7.4 Hz, 3H); IR (film) ν_max 3452, 2926, 1737, 1503, 1458, 1230, 1040 cm⁻¹; HRESI-TOF m/z 919.4936 (C₅₂H₆₆N₆O₉+H⁺, required 919.4964); [α]_D²³ −136 (c 0.03, CHCl₃).

Compound (R=20'-NHCO-4-phenylpiperidine) 56
Yield: 73%; Method 2. ¹H NMR (600 MHz, CDCl₃) δ 9.86 (br s, 1H), 8.01 (br s, 1H), 7.52 (d, J=8.0 Hz, 1H), 7.24-7.10 (m, 8H), 6.62 (s, 1H), 6.10 (s, 1H), 5.85 (dd, J=10.0, 4.3 Hz, 1H), 5.47 (s, 1H), 5.30 (d, J=10.1 Hz, 1H), 4.55 (br s, 1H), 4.33 (d, J=13.5 Hz, 1H), 4.26 (d, J=13.0 Hz, 1H), 3.87-3.83 (m, 1H), 3.81-3.77 (m, 1H), 3.80 (s, 6H), 3.74 (s, 1H), 3.56 (s, 3H), 3.39-3.35 (m, 2H), 3.31-3.25 (m, 2H), 3.20-3.16 (m, 2H), 3.04-2.95 (m, 2H), 2.83 (d, J=16.1 Hz, 1H), 2.71 (s, 3H), 2.67 (s, 1H), 2.61 (d, J=13.9 Hz, 1H), 2.47-2.40 (m, 2H), 2.25 (d, J 14.2 Hz, 1H), 2.20-2.15 (m, 1H), 2.11 (s, 3H), 1.94-1.87 (m, 3H), 1.84-1.72 (m, 5H), 1.37-1.22 (m, 6H), 0.81 (t, J=7.4 Hz, 3H), 0.78 (t, J=7.4 Hz, 3H); IR (film) ν_max 3442, 2922, 1738, 1503, 1233, 1038 cm⁻¹; HRESI-TOF m/z 997.5432 (C₅₈H₇₂N₆O₉+H⁺, required 997.5433); [α]_D²³ −22 (c 0.05, CHCl₃).

Compound (R=20'-NHCO-1,2,3,4-tetrahydroisoquinoline) 57
Yield: 58%; Method 2. ¹H NMR (600 MHz, CDCl₃) δ 9.86 (br s, 1H), 8.00 (br s, 1H), 7.48 (d, J=8.0 Hz, 1H), 7.17-7.13 (m, 5H), 7.11-7.09 (m, 2H), 6.63 (s, 1H), 6.11 (s, 1H), 5.85 (dd, J=10.1, 4.1 Hz, 1H), 5.47 (s, 1H), 5.30 (d, J=10.2 Hz, 1H), 4.77-4.71 (m, 2H), 4.57 (s, 1H), 3.94-3.89 (m, 1H), 3.81 (s, 3H), 3.80 (s, 3H), 3.74 (s, 1H), 3.74-3.71 (m, 2H), 3.52 (s, 3H), 3.40-3.36 (m, 2H), 3.30 (td, J=9.5, 4.8 Hz, 1H), 3.24-3.20 (m, 2H), 3.14-3.10 (m, 2H), 2.95-2.94 (m, 2H), 2.83 (d, J=16.1 Hz, 1H), 2.71 (s, 3H), 2.67 (s, 1H), 2.62 (d, J=13.8 Hz, 1H), 2.47-2.41 (m, 1H), 2.40 (d, J=13.3 Hz, 1H), 2.27 (d, J=14.2 Hz, 1H), 2.21-2.16 (m, 1H), 2.11 (s, 3H), 2.05 (s, 1H), 1.84-1.74 (m, 4H), 1.39-1.25 (m, 4H), 0.81 (t, J=7.4 Hz, 3H), 0.75 (t, J=7.5 Hz, 3H); IR (film) ν_max 2922, 2852, 1737, 1617, 1459, 1227, 1039 cm⁻¹; HRESI-TOF m/z 969.5102 (C₅₆H₆₈N₆O₉+H⁺, required 969.5120); [α]_D²³ +25 (c 0.07, CHCl₈).

Compound (R=20'-NHCO-isoindoline) 58
Yield: 45%; Method 2. ¹H NMR (600 MHz, CDCl₃) δ 9.86 (br s, 1H), 7.99 (br s, 1H), 7.47 (d, J=7.9 Hz, 1H), 7.33-7.31 (m, 2H), 7.29-7.26 (m, 2H), 7.15-7.12 (m, 1H), 7.10-7.07 (m, 2H), 6.62 (s, 1H), 6.11 (s, 1H), 5.85 (dd, J=10.4, 4.7 Hz, 1H), 5.47 (s, 1H), 5.29 (d, J=10.6 Hz, 1H), 4.92-4.85 (m, 4H), 4.41 (br s, 1H), 3.95 (t, J=13.6 Hz, 1H), 3.82 (s, 3H), 3.80 (s, 3H), 3.75 (s, 1H), 3.51 (s, 3H), 3.41-3.36 (m, 2H), 3.32-3.16 (m, 5H), 2.83 (d, J=16.1 Hz, 1H), 2.72 (s, 3H), 2.66 (s, 1H), 2.46-2.43 (m, 2H), 2.33-2.29 (m, 1H), 2.21-2.16 (m, 2H), 2.11 (s, 3H), 2.05 (s, 1H), 1.85-1.71 (m, 4H), 1.35-1.25 (m, 4H), 0.80 (t, J=7.3 Hz, 6H); IR (film) ν_max 3468, 2928, 1737, 1500, 1460, 1228, 1040 cm⁻¹; HRESI-TOF m/z 955.4952 (C₅₅H₆₆N₆O₉+H⁺, required 955.4964); [α]_D²³ −56 (c 0.03, CHCl₈).

Compound (R=20'-NHCO-5-methoxy-isoindoline) 59
Yield: 64%; Method 2. ¹H NMR (600 MHz, CDCl₃) δ 9.86 (br s, 1H), 8.00 (br s, 1H), 7.48 (d, J=8.0 Hz, 1H), 7.20 (d, J=8.4 Hz, 1H), 7.15-7.12 (m, 1H), 7.10-7.07 (m, 2H), 6.85-6.82 (m, 2H), 6.63 (s, 1H), 6.11 (s, 1H), 5.85 (dd, J=10.2, 4.5 Hz, 1H), 5.47 (s, 1H), 5.29 (d, J=10.1 Hz, 1H), 4.88-4.78 (m, 4H), 4.39 (br s, 1H), 3.97-3.92 (m, 1H), 3.87 (d, J 7.3 Hz, 1H), 3.82 (s, 3H), 3.80 (s, 6H), 3.74 (s, 1H), 3.50 (s, 3H), 3.42-3.23 (m, 5H), 3.18-3.15 (m, 2H), 2.71 (s, 3H), 2.66 (s, 1H), 2.63 (d, J=13.7 Hz, 1H), 2.47-2.39 (m, 2H), 2.30-2.27 (m, 1H), 2.21-2.16 (m, 2H), 2.11 (s, 3H), 1.85-1.76 (m, 6H), 1.35-1.28 (m, 2H), 0.80 (t, J=7.3 Hz, 3H), 0.79 (t, J 7.3 Hz, 3H); IR (film) ν_max 3461, 2926, 1737, 1617, 1460, 1236, 1035, 741 cm$^{-1}$; HRESI-TOF m/z 985.5061 ($C_{56}H_{68}N_6O_{10}$+H$^+$, required 985.5069); $[\alpha]_D^{23}$-27 (c 0.2, CHCl$_3$).

Cell Growth Inhibition Assay.

Compounds were tested for their cell growth inhibition of L1210 (ATCC #CCL-219, mouse lymphocytic leukemia, see Supporting Information) cells, HCT116 (ATCC #CCL-247, human colorectal carcinoma) cells, and HCT116/VM46 (a vinblastine-resistant strain of HCT116) cells in culture. A population of cells (>1×10$^6$ cells/mL as determined with a hemocytometer) was diluted with an appropriate amount of Dulbecco-modified Eagle Medium (DMEM, Gibco) containing 10% fetal bovine serum (FBS, Gibco) to a final concentration of 30,000 cells/mL.

To each well of a 96-well plate (Corning Costar), 100 μL of the cell-media solution was added with a multichannel pipette. The cultures were incubated at 37° C. in an atmosphere of 5% CO$_2$ and 95% humidified air for 24 hours. The test compounds were added to the plate as follows: test substances were diluted in DMSO to a concentration of 1 mM and 10-fold serial dilutions were performed on a separate 96-well plate. Fresh culture medium (100 μL) was added to each well of cells to constitute 200 μL of medium per well followed by 2 μL of each test agent. Compounds were tested in duplicate (n=2-8 times) at six concentrations between 0-1,000 nM or 0-10,000 nM. Following addition, cultures were incubated for an additional 72 hours.

A phosphatase assay was used to establish the IC$_{50}$ values as follows: the media in each cell was removed and 100 μL of phosphatase solution (100 mg phosphatase substrate in 30 mL 0.1 M NaOAc, pH 5.5, 0.1% Triton X-100 buffer) was added to each well. The plates were incubated at 37° C. for either 5 minutes (L1210) or 15 minutes (HCT116 and HCT116/VM46). After the given incubation time, 50 μL of 0.1 N NaOH was added to each well and the absorption at 405 nm was determined using a 96 well plate reader. As the absorption is directly proportional to the number of living cells, the IC$_{50}$ values were calculated and the reported values represent of the average of 4-16 determinations (SD±10%).

Tubulin Binding Competition Assay.

The competitive displacement of $^3$H-vinblastine (obtained from Moravek Biochemicals, Inc.) from purified porcine tubulin (tubulin and general tubulin buffer obtained from Cytoskeleton, Inc.) was measured using a procedure previously described. [Owellen et al., *Biochem. Pharmacol.* 1977 26:1213-1219.] As described, a 100 μL sample of tubulin solution diluted with 850 μL buffer was incubated with 25 μL of 7.2×10$^{-5}$ M $^3$H-vinblastine for 15 minutes at 37° C., after which 25 μL of 7.2×10$^{-5}$ M unlabeled alkaloid was added and incubation continued for 60 minutes. Tubulin-bound $^3$H-vinblastine was adsorbed onto DEAE filter paper and counted directly. Millipore Steriflip® filter units were used to wash the filter paper with buffer under mild suction.

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A vinca alkaloid compound or pharmaceutically acceptable salt thereof that is substituted at the 20'-position with a urea or thiourea group in which a proximal nitrogen atom that is directly bonded to the 20'-carbon atom is secondary and a distal nitrogen atom that is unsubstituted, or contains one or two substituents, wherein said one or two substituents are independently selected from the group consisting of a) a straight or branched chain hydrocarbyl group that has 1 to about 6 carbon atoms that is free of quaternary carbon atoms, b) an aromatic or aliphatic carbocyclic or heterocyclic ring structure that contains one or two rings, up to twelve ring atoms, and up to four ring atoms that are independently nitrogen, oxygen or sulfur, said ring structure being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, c) an aralkyl or heteroaralkyl group containing 5 or 6 ring atoms of which up to three ring atoms can independently be nitrogen, oxygen or sulfur and 1-3 carbons in the alkyl portion, said ring structure being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, and d) two substituents on the distal nitrogen atom together with that distal nitrogen atom form a single 5- or 6-membered ring or a fused ring system containing two rings, each of which can contain a 5- or 6-members and can also contain one or two additional ring hetero atoms that can independently be nitrogen, oxygen or sulfur said ring or ring system being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, said vinca alkaloid compound optionally containing a 10'-fluoro substituent and having a distal nitrogen atom that is unsubstituted only when said 10'-fluoro substituent is present.

2. The vinca alkaloid compound or salt thereof according to claim 1 that is a 20'-substituted vinblastine, vincristine or vindesine.

3. The vinca alkaloid compound or salt thereof according to claim 1 whose 20'-substituent is a urea.

4. The vinca alkaloid compound or salt thereof according to claim 3 whose distal urea nitrogen atom contains one substituent.

5. The vinca alkaloid compound or salt thereof according to claim 4 whose one substituent is a straight or branched chain hydrocarbyl group that has 1 to about 6 carbon atoms.

6. The vinca alkaloid compound or salt thereof according to claim 4 whose one substituent is an aromatic or aliphatic carbocyclic or heterocyclic ring structure that contains one or two rings, up to twelve ring atoms, and up to four ring atoms that are independently nitrogen, oxygen or sulfur.

7. The vinca alkaloid compound or salt thereof according to claim 6 whose one substituent is an aliphatic carbocyclic ring structure containing one ring containing 3-6 carbons.

8. The vinca alkaloid compound or salt thereof according to claim 6 whose one substituent is an aromatic ring structure that contains one or two rings.

9. The vinca alkaloid compound or salt thereof according to claim 8 whose aromatic ring structure contains a single substituent group.

10. The vinca alkaloid compound or salt thereof according to claim 3, wherein two substituents on the distal urea nitrogen atom together with that distal nitrogen atom form a single 5- or 6-membered ring or a fused ring system containing two rings, each of which can contain a 5- or 6-members and can also contain one or two additional ring hetero atoms that can independently be nitrogen, oxygen or sulfur, said ring or ring system being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof.

11. The vinca alkaloid compound or salt thereof according to claim 10, wherein said two substituents on the distal urea nitrogen atom together with that distal nitrogen atom form a 6-membered ring.

12. The vinca alkaloid compound or salt thereof according to claim 10, wherein said two substituents on the distal urea nitrogen atom together with that distal nitrogen atom form a 5-membered ring.

13. The vinca alkaloid compound or salt thereof according to claim 10, wherein said two substituents on the distal urea nitrogen atom together with that distal nitrogen atom form a fused ring system containing two rings, each of which can contain a 5- or 6-members and can also contain one or two additional ring hetero atoms that can independently be nitrogen, oxygen or sulfur.

14. The vinca alkaloid compound or salt thereof according to claim 1 that corresponds in structure to Formula I below:

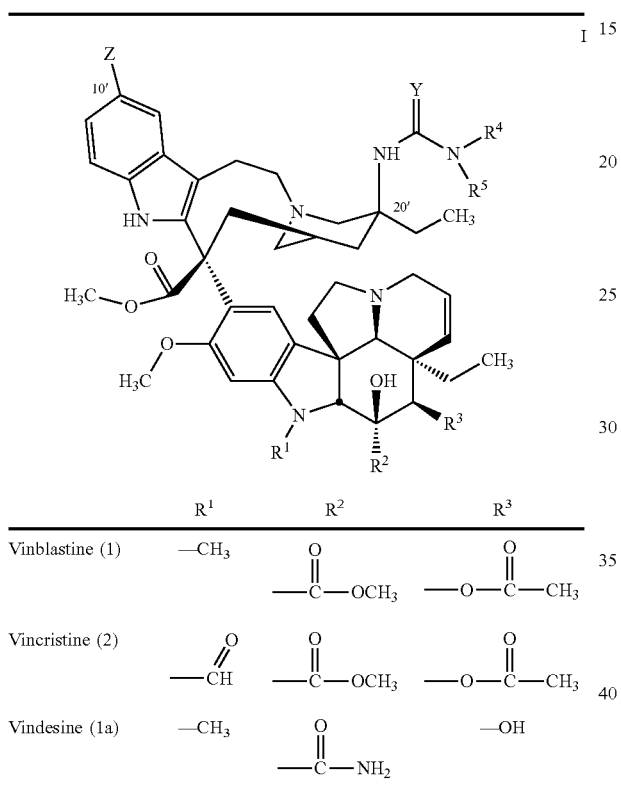

| | $R^1$ | $R^2$ | $R^3$ |
|---|---|---|---|
| Vinblastine (1) | —CH$_3$ | —C(O)—OCH$_3$ | —O—C(O)—CH$_3$ |
| Vincristine (2) | —CH(O) | —C(O)—OCH$_3$ | —O—C(O)—CH$_3$ |
| Vindesine (1a) | —CH$_3$ | —C(O)—NH$_2$ | —OH | where Z is H or F,
Y is O or S, and
$R^4$ and $R^5$ are independently selected from the group consisting of hydrido, or a) a straight or branched chain hydrocarbyl group that has 1 to about 6 carbon atoms that is free of tertiary or quaternary carbon atoms, b) an aromatic or aliphatic carbocyclic or heterocyclic ring structure that contains one or two rings, up to twelve ring atoms, and up to four ring atoms that are independently nitrogen, oxygen or sulfur, said ring structure being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, c) an aralkyl or heteroaralkyl group containing 5 or 6 ring atoms of which up to three ring atoms can independently be nitrogen, oxygen or sulfur and 1-3 carbons in the alkyl portion, said ring structure being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof, and d) two substituents on the distal nitrogen atom together with that distal nitrogen atom form a single 5- or 6-membered ring or a fused ring system containing two rings, each of which can contain a 5- or 6-members and can also contain one or two additional ring hetero atoms that can independently be nitrogen, oxygen or sulfur said ring or ring system being optionally substituted with 1, 2 or 3 substituents selected from the group consisting of $C_1$-$C_6$-hydrocarbyl, $C_1$-$C_6$-hydrocarbyloxy, phenyl, halogen, perfluoro-$C_1$-$C_6$-hydrocarbyl, perfluoro-$C_1$-$C_6$-hydrocarbyloxy, nitro and mixtures thereof,
with the proviso that $R^4$ and $R^5$ are only both hydrido when Z is F.

15. The vinca alkaloid compound or salt thereof according to claim 14, wherein Z is F.

16. The vinca alkaloid compound or salt thereof according to claim 15 that corresponds in structure to the structural formula below.

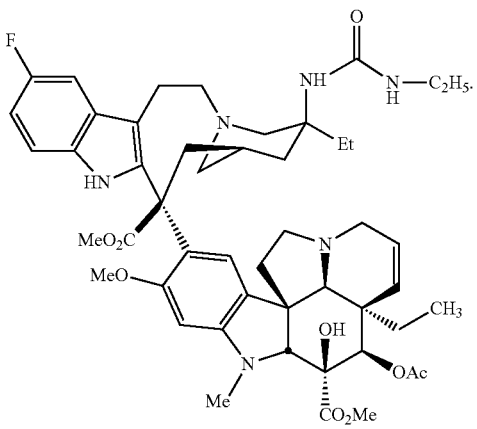

17. A pharmaceutical composition that comprises a cancerous cell proliferation-inhibiting amount of a 20'-urea-substituted vinca alkaloid compound of claim 1 or a pharmaceutically acceptable salt thereof dissolved or dispersed in a physiologically acceptable carrier.

18. A method of inhibiting the growth of cancerous cells that comprises contacting said cancerous cells with a cancerous cell proliferation-inhibiting amount of a 20'-urea- or thiourea-substituted vinca alkaloid compound of claim 1 or a pharmaceutically acceptable salt thereof.

19. The method according to claim 18, wherein said cancerous cells are contacted a plurality of times.

20. The method according to claim 18, wherein said cancerous cells are contacted in vitro.

21. The method according to claim 18, wherein said contacted cancerous cells are leukemia cells.

22. The method according to claim 18, wherein said contacted cancerous cells are carcinoma cells.

23. The method according to claim 22, wherein said contacted carcinoma cells are resistant to vinblastine.

* * * * *

UNITED STATES PATENT AND TRADEMARK OFFICE
CERTIFICATE OF CORRECTION

PATENT NO. : 9,611,271 B2
APPLICATION NO. : 14/648624
DATED : April 4, 2017
INVENTOR(S) : Dale Boger Page 1 of 1

It is certified that error appears in the above-identified patent and that said Letters Patent is hereby corrected as shown below:

In the Specification

Column 1, Lines 13-18, the paragraph GOVERNMENTAL SUPPORT should be changed to:
-- STATEMENT OF GOVERNMENT LICENSE RIGHTS
This invention was made with government support under grant numbers CA115526, CA165303, and CA042056 awarded by the National Institutes of Health. The government has certain rights in the invention. --

Signed and Sealed this
Fifth Day of May, 2020

Andrei Iancu
*Director of the United States Patent and Trademark Office*